United States Patent [19]
Greenberg et al.

[11] Patent Number: 5,907,078
[45] Date of Patent: May 25, 1999

[54] TRANSGENIC MOUSE MODEL FOR PROSTATE CANCER

[76] Inventors: Norman M. Greenberg, 8450 Cambridge, Suite 2199, Houston, Tex. 77054; Robert J. Matusik, 39 Paradise Drive, Winnipeg, Manitoba, Canada, R3R 1K9; Jeffrey M. Rosen, 3815 Grenoch La., Houston, Tex. 77060

[21] Appl. No.: 08/414,335

[22] Filed: Mar. 31, 1995

Related U.S. Application Data

[63] Continuation-in-part of application No. 08/351,365, Dec. 9, 1994.

[51] Int. Cl.$^6$ .................................................. C12N 15/00
[52] U.S. Cl. ............... 800/2; 800/DIG. 1; 800/DIG. 2; 800/DIG. 3; 800/DIG. 4; 536/23.1; 536/23.5; 435/320.1; 435/172.3
[58] Field of Search ................... 424/93.1; 435/240.2, 435/325; 514/44; 800/2, DIG. 4; 536/23.1

[56] References Cited

U.S. PATENT DOCUMENTS 5,162,215 11/1992 Bosselman et al. .................. 435/172.3
5,545,808 8/1996 Hew et al. .................................. 800/2

OTHER PUBLICATIONS

Pursel et al, Genetic Engineering of Livestock, Science vol. 244 pp. 1281–1288, Jun. 16, 1989.
Adams, J.M., & Cory, S. (1991). Transgenic models of tumor development. Science, 254, 1161–1167.
Aprikian, A.G., Sarkis, A.S., Fair, W.R., Zhang, Z.–F., Fuks, Z., & Cordon–Caro, C. (1994). Immunohistochemical determination of p53 protein nuclear accumulation in prostatic adenocarcinoma. Journal Urology, 151, 1276–1280.
Berry, S.J., Coffey, D.S., & Ewing, L.L. (Ed.). (1984). A comparison of human and canine benign prostatic hyperplasia. Berlin: Congressduck.
Bogden. A.E., Taylor, J.E., Moreau, J.P., & Coy, D.H. (1990). Treatment of R–3327 prostate tumors with a somatostatin analogue (somatuline) as adjuvant therapy following surgical castration. Cancer Res., 50(9), 2646–2650.
Bookstein, R., Rio, P., Madreperla, S.A., Hong, F., Allred, C., Grizzle, W.E., & Lee, W.H. (1990). Promoter deletion and loss of retinoblastoma gene expression in human prostate carcinoma. Proc. Natl. Acad. Sci. USA 87(19), 7762–7766.

(List continued on next page.)

Primary Examiner—Jasemine C. Chambers
Assistant Examiner—Deborah J.R. Clark
Attorney, Agent, or Firm—Sim & McBurney

[57] ABSTRACT

Several lines of transgenic mice have been generated using the prostate-specific rat probasin (PB) gene promoter to drive expression of the SV40 T antigen (Tag) coding region. Mice expressing high levels of the transgene specifically display progressive forms of prostatic cancer that histologically resemble human prostate cancer ranging from mild prostatic intraepithelial neoplasia (PIN) to large multinodular malignant adenocarcinoma with metastasis. Adenocarcinomas of the prostate have been detected as early as 10 weeks of age with extracapsular extension (ECE) and seminal vesicle invasion (SVI). Immunohistochemical analysis of tumor tissue has demonstrated that dorsolateral prostate-specific secretory proteins were confined to well differentiated ductal epithelial cells adjacent to, or within the poorly differentiated tumor mass. Prostate tumors in the mice also display elevated levels of nuclear p53, and a decreased heterogenous pattern of androgen receptor (AR) expression as observed in advanced human prostate cancer. The establishment of breeding lines of transgenic mice that reproducibly develop prostate cancer with metastasis provides a unique animal model system to study the molecular basis of transformation of normal prostatic cells and the factors influencing the progression to metastatic prostate cancer.

10 Claims, 60 Drawing Sheets

OTHER PUBLICATIONS

Bosland, M.C., & Prinsen, M.K. (1990). Induction of dorsolateral prostate adenocarcinoma and other accessory sex gland lesions in male wistar rats by a single administration of N–methyl–N–nitrosourea, 7,12–dimethylbenz(a)anthracene, and 3,2'–dimethyl–4–aminobiphenyl after sequential treatment with cyproterone acetate and testosterone propionate. Cancer Res., 50, 691–699.

Bosland, M.C., Prinsen, M.K., Dirksen, T.J.M., & Spit, B.J. (1990). Characterization of adenocarcinoma of the dorsolateral prostate induced in wistar rats by N–methyl–N–nitrosourea, 7,12, dimethylbenz(a)anthracene, and 3,2'–dimethyl–4–aminobiphenyl, following sequential treatment with cyproterone acetate and testosterone propionate. Cancer Res., 50, 700–709.

Brinster, R.L., Chen, H.Y., Messing, A., Van Dyke, T., Levine, A.J., & Palmiter, R.D. (1984). Transgenic mice harboring SV40 T–antigen genes develop characteristic brain tumors. Cell, 37, 367–379.

Buttyan, R., & Slawin, K. (1993). Rodent models for targeted oncogenesis of the prostate gland. Cancer and Metastasis Rev., 12, 11–19.

Carroll, A.G., Voeller, H.J., Sugars, L. & Gelmann, E.P. (1993). p53 oncogene mutations in three human prostate cancer cell lines. Prostate, 23(2), 123–134.

Choi, Y., Lee, I., & Ross, S.R. (1988). Requirement for the simian virus 40 small tumor antigen in tumorigenesis in transgenic mice. Mol. Cell Biol., 8 (8), 3382–3390.

Cooke, D.B., Quarmby, V.E., Mickey, D.D., Isaacs, J.T., & French, F.S. (1988). Oncogene expression in prostate cancer: dunning r3327 rat dorsal prostatic adenocarcinoma system. Prostate, 13(4), 263–272.

DeCaprio, J.A., Ludlow, J.W., Figge, J., Shew, J.–Y., Huang, C.–M., Lee, W.–H., Marsilio, E., Paucha, E., & Livingston, D.M. (1988). SV40 large tumor antigen forms a specific complex with the product of the retinoblastoma susceptibility gene. Cell 17, 275–283.

Dodd, J.G., Sheppard, P.C., & Matusik, R.J. (1983). Characterization and cloning of highly abundant mRNAs of the rat dorsal prostate. J. Biol. Chem., 258, 10731–10737.

Donjacour, A.A., Rosales, A., Higgins, S.J., & Cunha, G.R. (1990). Characterization of antibodies to androgen–dependent secretory proteins of the mouse dorsolateral prostate. Endocrinology, 1343–1354.

Frost, J.A., Alberts, A.S., Sontag, E., Guan, K., Mumby, M.C., & Feramisco, J.R. (1994). Simian virus 40 small t antigen cooperates with mitogen activated kinases to stimulate AP–1 activity. Molecular and Cellular Biol., 14, 6244–6252.

Greenberg, N.M., DeMayo, F.J., Sheppard, P.C., Barrios, R., Lebovitz, R., Finegold, M., Angelopolou, R., Dodd, J.G., Duckworth, M.L., Rosen, J.M., & Matusik, R.J. (1994). The rat probasin gene promoter directs hormonally– and developmentally–regulated expression of a heterologous gene specifically to the prostate in transgenic mice. Mol. Endocrinol., 8, 230–239.

Habenicht, U.F., el–Etreby, M.F., Lewis, R., Ghoniem, & Roberts, J. (1989). Induction of metachromasia in experimentally induced hyperplastic/hypertrophic changes in the prostate of the cynomolgus monkey (*Macaca fasciculari*). J. Urol., 142, 1624–1626.

Hanahan, D. (1985). Heritable formation of pancreatic β–cell tumors in transgenic mice expressing recombinant insulin/simian virus 40 oncogenes. Nature, 315, 115–122.

Husmann, D.A., Wilson, C.M., McPhaul, M.J., Tilley, W.D., & Wilson, J.D. (1990). Antipeptide antibodies to two distinct regions of the androgen receptor localize the receptor protein to the nuclei of target cells in the rat and human prostate. Endocrinology, 126, 2359–2368.

Isaacs, W.B., Carter, B.S., & Ewing, C.M. (1991). Wild–type p53 suppresses growth of human prostate cancer cells containing mutant p53 alleles. Cancer Res., 51(17), 4716–4720.

Lane, D.P., & Crawford, L.V. (1979). T–antigen is bound to host proteins in SV40–transformed cells. Nature, 278, 261–263.

Levine, A.J., & Momand, J. (1990). Tumor suppressor genes: the p53 and retinoblastoma sensitivity genes and gene products. Biochem. Biophys. Acta. 1032(1), 119–136.

Levine, A.J., Momand, J., & Finlay, C.A. (1991). The p53 tumor suppressor gene. Nature, 351(6326), 453–456.

Linzer, D.I.H., & Levine, A.J. (1979). Characterization of a 54K dalton cellular SV40 tumor antigen present in SV40–transformed cells and uninfected embryonal carcinoma cells. Cell, 17, 43–52.

Maroulakou, I.G., Anver, M., Garrett, L. & Green, J.E. (1994). Prostate and mammary adenocarcinoma in transgenic mice carrying a C3(1) simian virus 40 large tumor antigen fusion gene. Proc. Natl. Acad. Sci. USA, 91, 11236–11240.

Matusik, R.J., Kreis, C., McNicol, P., Sweetland, R., Mullin, C., Fleming, W.H., & Dodd, J.G. (1986). Regulation of prostatic genes: Roles of androgens and zinc in expression. J. Biochem. Cell Biology, 64, 601–607.

Muller, W.J., Lee, F.S., Dickson, C., Peters, G., Pattengale, P., & Leder, P. (1990). The int–2 gene product acts as an epithelial growth factor in transgenic mice. EMBO J., 9(3), 907–913.

Noble, R.L. (1977). The development of prostatic adenocarcinoma in Nb rats following prolonged sex hormone administration. Cancer Research, 37, 1927–1931.

Ornitz, D.M., Moreadith, R.W., & Leder, P. (1991). Binary system for regulating transgene expression in mice: Targeting int–2 gene expression with yeast GAL4/UAS control elements. Proc. Natl. Acad. Sci. USA, 88, 698–702.

Pallas, D.C., Shahrik, L.K., Martin, B.L., Jaspers, S., Miller, T.B., Brautigan, D.L., & Roberts, T.M. (1990). Polyoma small and middle T antigens and SV40 small t antigen form stable complexes with protein phosphatase 2A. Cell, 60, 167–176.

Pollard, M. (1973). Spontaneous adenocarcinomas in aged germfree Wistar rats. J. Natl. Cancer Inst., 51, 1235–1241.

Pollard M., & Luckert, P.H. (1987). Autochthonous prostate adenocarcinomas in Lobund–Wistar rats: a model system. Prostate, 11(3), 219–227.

Pollard, M., Luckert, P.H. & Snyder, D.L,. (1989). The promotional effect of testosterone on induction of prostate cancer in MNU–sensitized L–W rats. Cancer Lett, 45(3), 209–212.

Quartin, R.S., Cole, C.N., Pipas, J.M., & Levine, A.J. (1994). The amino–terminal functions of the simian virus 40 large T antigen are required to overcome wild–type p53–mediated growth arrest of cells. J. Virol., 68(3), 1334–1341.

Rennie P.S., Bruchovsky, N., Leco, K.J., Sheppard, P.C., McQueen, S.A., Cheng, H., Snoek, R., Hamel, A., Bock, M.E., MacDonald, B.S., Nickel, B.E., Chang, C., Liao, S., Cattini, P.A., & Matusik, R.J. (1993). Characterization of two cis–acting DNA elements involved in the androgen regulation of the probasin gene. Mol. Endocrinol., 7, 23–36.

Riegman P.H., Vlietstra, R.J., van, d.K.J.A., Romijn, J.C., & Trapman, J. (1989). Characterization of the prostate–specific antigen gene: a novel human kallikrein–like gene. Biochem. Biophys. Res. Commun. 159(1), 95–102.

Rubin, S.J., Hallahan, D.E., Ashman, C.R., Brachman, D.G., Beckett, M.A., Virudachalam, S., Yandell, D.W., & Weichselbaum, R.R. (1991). Two prostate carcinoma cell lines demonstrate abnormalities in tumor suppressor genes. J. Surg. Oncol. 46(1). 31–36.

Sadi, M.V., & Barrack, E.R. (1993). Image analysis of androgen receptor immunostaining in metastatic prostate cancer. Heterogeneity as a predictor of response to hormonal therapy. Cancer, 71, 2574–2580.

Schaffner, D.L., Barrios, R., Shaker, M., Rajagopalan, S., Huang, S., Tindall, D.J., Young, C.Y.F., Overbeek, P.A., Lebovitz, R.M., & Lieberman, M.W. (1994). Transgenic mice carrying a PSAras T24 hybrid gene develop salivary gland and GI tract neoplasms. Laboratory Investigation, in press.

Shain, S.A., McCullough, B., Nitchuk, M., & Boesel, R.W., (1977). Prostate carcinogenesis in the AXC rat. Oncology, 34(3), 114–122.

Shain, S.A., McCullough, B., & Segaloff, A. (1975). Spontaneous adenocarcinomas of the ventral prostate of aged AXC rats. J. Natl. Cancer Inst., 55(1), 177–180.

Shaulsky, G., Goldfinger, N., Tosky, M.S., Levine, A.J., & Rotter, V. (1991). Nuclear localization is essential for the activity of p53 protein. Oncogene, 6(11), 2055–2065.

Shirai, T., Fukushima, S., Ikawa, Y., & Ito, N. (1986). Induction of prostate carcinoma in situ at high incidence in F344 rats by a combination of 3,2'–dimethyl–4–aminobiphenyl and ethinyl estradiol. Cancer Res., 46, 6423–6426.

Silverberg, E.S., Boring, C.C. & Squires, T.S. (1990). Cancer Statistics. CA Cancer J. Clin. 40, 9–26.

Slawin, K., Kadmon, D., Park, S.H., Scardino, P.T., Anzano, M., Sporn, M.B., & Thompson, T.C. (1993). Dietary fenretinide, a synthetic retinoid, decreases the tumor incidence and the tumor mass of ras+myc–induced carcinomas in the mouse prostate reconstitution model system. Cancer Res., 53(19), 4461–4465.

Smith, M.S., Lechago, J., Wines, D.R., MacDonald, R.J., & Hammer, R.E. (1992). Tissue–specific expression of kallikrein family transgenes in mice and rats. DNA Cell Biol., 11(5), 345–358.

Sweetland, R., Sheppard, P.C., Dodd, J.G., & Matusik, R.J. (1988). Post–castration rebound of an androgen regulated prostatic gene. Mol. Cell Biochem. 84, 3–15.

Thalman, G.N., Anezinis, P.E., Chang, S.–M., Zhau, H.E., Kim, E., Hopwood, V.L., Pathak, S., von Eschenbach, A.C., & Chung, L.W.K. (1994). Androgen–independent cancer progression and bone metastasis in the LnCaP model of human prostate cancer. Cancer Research, 54, 2577–2581.

Thompson, T.C., Kadmon, D., Timme, T.L., Merz, V.W., Egawa, S., Krebs, T., Scardino, P.T., & Park, S.H. (1991). Experimental oncogene induced prostate cancer. Cancer Surv. 11, 55–71.

Thompson, T.C., Timme, T.L., Kadmon, D., Park, S.H., Egawa, S., & Yoshida, K. (1993a). Genetic predisposition and mesenchymal–epithelial interactions in ras+myc–induced carcinogenesis in reconstituted mouse prostate. Molecular Carcinogenesis, 7(3), 165–179.

Thompson, T.C., Truong, L.D., Timme, T.L., Kadmon, D., McCune, B.K., Flanders, K.C., Scardino, P.T., & Park, S.H. (1993b). Transgenic models for the study of prostate cancer. Cancer 71(3 Suppl), 1165–1171.

Thompson, T.T., Southgate, J., Kitchener, G., & Land, H. (1989). Multistage carcinogenesis induced by ras and myc oncogenes in a reconstituted organ. Cell, 56, 917–930.

Tilley, W.D., Lim–Tio, S.S., Horsfall, D.J., Aspinall, J.O., Marshall, V.R., & Skinner, J.M. (1994). Detection of discrete androgen receptor epitopes in prostate cancer by immunostaining: Measurement by color video image analysis. Cancer Research, 54, 4096–4102.

Timme, T.L., Park, S.H., Ren, C., Eastham, J.A., Baley, P.A., Kadmon, D., Donehower, L.A., & Thompson, T.C. (1994). The use of a novel mouse model for prostate cancer metastasis to analyze the role of p53 gene loss and alteration during progression. AACR Proceedings, 35, 584.

Tutrone, R.F.J., Ball, R.A., Ornitz, D.M., Leder, P. & Richie, J.P. (1993). Benign prostatic hyperplasia in a transgenic mouse: a new hormonally sensitive investigatory model. J. Urology, 149, 633–639.

Tzeng, Y.J., Guhl, E., Graessmann, M., & Graessmann, A. (1993). Breast cancer formation in transgenic animals induced by the whey acidic protein SV40 T antigen (WAP–SV–T) hybrid gene. Oncogene, 8(7), 1965–1971.

van, S.G.J., & Schroder, F.H. (1988). Androgen–dependent human prostate cancer in nude mice. The PC–82 tumor model. Am. J. Clin. Oncol., 2.

Waalkes, M.P., Rehm, S., Riggs, C.W., Bare, R.M., Devor, D.E., Poirer, L.A., Wenk, M.L., Henneman, J.R., & Balaschak, M.S. (1988). Cadmium carcinogenesis in male Wistar [Crl:(WI)BR] rats: dose–response analysis of tumor induction in the prostate and testes and at the injection site. Cancer Res., 48, 4656–4663.

AAGCTTCCACAAGTGCATTTAGCCTCTCCCAGTATTGCTGATGAATCCACAGTTCAGGTTC

AATGGCGTTCAAAACTTGATCAAAAATGACCAGACTTTATATTCTTACACCAACATCTAT

CTGATTGGAGGAATGGATAATAGTCATCATGTTTAAACATCTACCATTCCAGTTAAGAAA

ATATGATAGCATCTTGTTCTTAGTCTTTTTCTTAATAGGGACATAAAGCCCACAAATAAA

AATATGCCTGAAGAATGGGACAGGCATTGTCCATGCCTAGTAAAGTACTCCAA

FIG.8B

```
                     -101  -95                         -82      -75
                       *    *                           *        *
GAACCTATTTGTATACTAGATGACACAATGTCTGTGTACAACTGCCAACTGGGA

-48                           -27
             *                              *
TGCAAGACACTGCCCAATCATCCTGAAAAGCAGCTATAAAAGCAGGAAGCTACT

+1                                     +28
  v*                                       *
CTGCACCTTGTCAGTGAGGTCCAGATACCTACAGAGCTCACACAGC ATG AGG GTC
                                               Met Arg Val
```

```
ATC CTC CTC CTG CTC ACA CTG GAT GTG CTA GGT GTC TCC AGT
Ile Leu Leu Leu Leu Thr Leu Asp Val Leu Gly Val Ser Ser

ATG ATG ACA GAC AAG AAT CTC AAA AAG AAG GTAGCAGAC
Met Met Thr Asp Lys Asn Leu Lys Lys Lys
```

FIG.9A (Linear) MAP of: SV40rev  check: 7624  from: 1 to: 5243

REVERSE-COMPLEMENT of: V01380  check: 7049  from: 1 to: 5243
LOCUS       SV40XX        5243 bp    DNA   circular  VRL    16-JUL-1993
DEFINITION  SV40 genome.
ACCESSION   V01380
KEYWORDS    circular; direct repeat; genome; origin of replication.
SOURCE      Rhesus macaque polyomavirus. . . .

With 203 enzymes: *                      March 27, 1995 15:37 ..

```
    H                                                          H
B   Ca         C                        C              C       CA B  aC
s   Cve DM    Av M            M M       v CM           B   s   vvBsHevSS
a   jiI dn    li n             n n      i jn           s   e   irfaaIitt
J   eJI eI    uJ l            l l       J eI           R   I   JIaJeIJuy
I   III II    II I            I I       I II           I   I   IIIIIIIII
    //  /     /  /            / /       / /                    /// //
   CGCCTCGGCCTCTGAGCTATTCCAGAAGTGAGGAGGCTTTTTTGGAGGCCTAGGCTT
1  ----------+---------+---------+---------+---------+---------+  60
   GCGGAGCCGGAGACTCGATAAGGTCTTCATCACTCCTCCGAAAAAACCTCCGGATCCGAA
```

FIG.9B

```
                                                                                    C
             C                              H                                    CB C
             v    C  C                      i              H                     vsTAv
             i  n Av v      B         MDM   T              i                     iosli
             R  d li i  C   c         srn   n    f         T                     RfeuJ
             I  I I R B     c         eal   f    i         A                     IIII
             I  I I I I     I         III   I    I         v                     IIII  /

TTGCAAAAAGCTTTGCAAAGATGGATAAAGTTTAAACAGAGAGGAATCTTTGCAGCTAA
 61  ----+---------+---------+---------+---------+---------+  120
     AACGTTTTTCGAAACGTTTCTACCTATTTCAAATTTGTCTCTCCTTAGAAACGTCGATT
                           ↑
                           OPEN READING FRAME

S                                  E
     A  B                               c                        M
     v  a  B                            B   o                    n
     u  9  b  f                         S   s   S                l
     I  I  v  a                             c   p                I
     I  6  I  I                             R   I
        I  I                                a   I
                                            r
                                            I

TGGACCTTCTAGGTCTTGAAAGGAGTGCCTGGGGAATATTCCTCTGATGAGAAAGGCAT
121  ----+---------+---------+---------+---------+---------+  180
     ACCTGGAAGATCCAGAACTTTCCTCACGGACCCCCTTATAAGGAGACTACTCTTTCCGTA
```

FIG. 9C

```
         M D     C       C                       E
         D       F   V       i                   Mc    B                    B    M
         s r     o   k       R                   n o   s                    s    b
         e a     I   I       I                   l n   l                    e    o
         I I                                     I I   I                    R    I
                                                                            I    I
     ATTTAAAAAAATGCAAGGAGTTTCATCCTGATAAAGGAGGAGATGAAGAAAAATGAAGA
181  ---------+---------+---------+---------+---------+---------+  240
     TAAATTTTTTTACGTTCCTCAAAGTAGGACTATTTCCTCCTCTACTTCTTTTTACTTCT

M       B                     M                                      M    B
         b       s    R                b                                      n    s
         o       r    s                o                                      l    l
         I       G    a                I                                      I    I
         I       I    I                I
     AAATGAATACTCTGTACAAGAAAATGGAGTAAAAATATGCTCATCAACCTGACT
241  ---------+---------+---------+---------+---------+---------+  300
     TTTACTTATGAGACATGTTCTTTTACCTTCATTTTATACGAGTAGTTGGACTGA
```

FIG.9D

```
         S  C                     C              M            M                   E             C   C
         f  v                     Mv            D  Fb         s             c S S            v   i
         a  i                     n i           d  o o        e            o f c           B  s  R
         N  J                     l R           e  k I        I            R a r          s   b I
         I  I                     I I           I  I I                     I N F         b    I
                                                                             I I I      I
                                                           ▲ SPLICE DONOR "T"

TTGGAGGCTTCTGGGATGCAACTGAGGTATTTGCTTCTTCCTTAAATCCTGGTGTTGATG
301   ------+---------+---------+---------+---------+---------+  360
      AACCTCCGAAGACCCTACGTTGACTCCATAAACGAAGAAGGAATTTAGGACCACAACTAC

T                 T                                           C  C
         B   C             t                 t                          C           v  a
         R s  v           h    C   v         h    1    C               v N         i  c
         s r  i           1   vHDe l   v     1    1    1              i d         R  8
         a D  R           1   i a d 1   i    1    1    1             R e         I  I
         I I  I               J e e I   R    I    I    I              I I
                              I I I I   I

CAATGTACTGCAAACAATGGCCTGAGTGTGCAAAGAAAATGTCTGCTAACTGCATATGCT
361   ------+---------+---------+---------+---------+---------+  420
      GTTACATGACGTTTGTTACCGGACTCACGTTTCTTTTACAGACGATTGACGTATACGA
```

FIG.9E

```
                        M               N   T                        S
                        w   M   D       l   s   A   BR  a       M
                        o   n   e       a   p   l   s1Du    s
                        I   l   l       F   5   w   tep3        l
                        I   I   I       o   0   I   YAna    I
                                        I   k       IIII    I
                                        I   9       ////    I
                                        I   I
421 TGCTGTGCTTACTGAGGATGAAGCATGAAAATTATACAGGAAAGATCCACTTG 480
    ----+----+----+----+----+----+----+----+----+----+----+----+
    ACGACACGAATGACTCCTACTTCGTACTTTTAATATGTCCTTTCTAGGTGAAC B                   T   M                               S
        s                   a   w                               a
        t                   q   o                               u   D
        X                   I   I                               3   p
        I                                                       A   n
                                                                I   I
                                                                    I
481 TGTGGGTTGATTGCTACTGCTTCGATTGCTTTAGAATGTGGTTTGGACTTGATCTTTGTG 540
    ----+----+----+----+----+----+----+----+----+----+----+----+
    ACACCCAACTAACGATGACGAAGCTAACGAAATCTTACACCAAACCTGAACTAGAAACAC
```

FIG.9F

```
                                   MT            T
                                   as       T   s
                                   ep       s   p            S       MD     C
                             N     I4       p   5            f       sr     Av
                             l     I5       5   0            c       ea     li
                             a     II       9   9            I       II     uJ
                             I      /       I   I                     I     II
                             V                                               I
         AAGGAACCTTACTTCTGTGGTGTGACATAATTGGACACAAACTACCTACAGAGATTTAAAGC
  541    ----+----|----+----|----+----|----+----|----+----|----+----|  600
         TTCCTTGGAATGAAGACACCACCACTGTATTAACCTGTTTGATGGATGTCTCTAAATTTCG
                        T                                       T
                        s                                       t
                        p                                       h      T
                        A5                    M                 lH     s
                        p0         M          s                 liT    p 5
                        o9         s          e                 lnf    0 9
                        II         I          I                 Ifi    I
                        II                                      III
                         /                                        /
         STOP"T"  ▲ SPLICE DONOR"t"
         TCTAAG|GTAAATATAAAATTTTAAGTGTATAATGTGTTAAACTACTGATTCTAATTGTT
  601    ----+----|----+----|----+----|----+----|----+----|----+----|  660
         AGATTCCATTTATATTTTAAAAATTCACATATTACACAATTTGATGACTAAGATTAACAA
```

↱ SPLICE ACCEPTOR (BOTH)
     TGTGTATTTTAGATTCCAACCTATGGAAGAACTGATGAATGGGAGCAGTGGTGGAATGCCTTT
661  ----------+---------+---------+---------+---------+---------+  720
     ACACATAAAATCTAAGGTTGGATACCTTGACTACTTACCCTCGTCACCACCTTACGGAAA

M
              D   B bB  M              C            C  v  P
              d   c o f n              n            v  i  l
                  e c Ia l             l            i  J  e
                  I I II I             I            I  I  I
     AATGAGGAAAACCTGTTTTGCTCAGAAGAAATGCCATCTAGTGATGATGAGGCTACTGCT
721  ----------+---------+---------+---------+---------+---------+  780
     TTACTCCTTTTGGACAAAACGAGTCTTCTTTTACGGTAGATCACTACTACTCCGATGACGA
```

FIG.9H

```
     H          B                                              E            C                    E   M
     i          s                          E    M              a            j                    c   b
     n          e                          a    n              r            e                    o   o
     f          R                          r    l              I            P                    5   I
     I          I                          I    I              I            I                    7   I
                                                                                                  I
781  GACTCTCAACATTCTACTCCCTCCAAAAAGAAGAGAAGGTAGAAGACCCCAAGGACTTT
     CTGAGAGTTGTAAGATGAGGAGGTTTTTCTTCTTCCATCTCTTCTGGGTTCCTGAAA
                                                                                                       //

C
                                                                            T            a
                                           H                                t            c
                                           i    N                           h            c
                                           n    l    a P                    I            I   8
                                           f    I    I l    I e             I            I   I
                                           I    I    I I    I I             I            I   I

841  CCTTCAGAATTGCTAAGTTTTTTGAGTCATGCTGTGTTTAGTAATAGAACTCTTGCTTGC
     GGAAGTCTTAACGATTCAAAAAACTCAGTACGACACAAATCATTATCTTGAGAACGAACG
```

FIG.9I

```
                                                 B  T
                                              B  C  s
                                           B  s  C  p
                                        B  s  v  A  5
                                        B  b  v  s  0
                 M                      s  g  T  v  9
                 w                      b  v  I  v  I
                 o                      I  I     T
                 I                            \ /
    TTTGCTATTTACACCACAAAGGAAAAAGCTGCTATACAAGAAAATTATGAAAAA
901 ----------+---------+---------+---------+---------+---------+ 960
    AAACGATAAATGTGGTGTTTCCTTTTTCGACGTGACGATATGTTCTTTTAATACCTTTTT

M
                 a
                 e
         S       I   I
         s       I   I
         p       I   I
         I       I   I
    TATTCTGTAACCTTTATAAGTAGGCATAACAGTTATAATCATAACATAC

FIG.9J

```
         C       T                    M V                         T
         A v     s                    s s                         s
         l i     p                    s s                         p    R
         u J     M 5                  e p                         5    s
         I I     s 0                  I I                         0    a
                 e 9                  I I                         9    I
                 I I                                              I
                  /
1021     ACTCCACACAGGCATAGAGTGTCTGCTATTAATAACTATGCTCAAAAATTGTGTACCTTT  1080
         ----+----+----+----+----+----+----+----+----+----+----+----+
         TGAGGTGTGTCCGTATCTCACAGACGATAATTATTGATACGAGTTTTTAACACATGGAAA

M               S                C   A B   H B
                                         s               s                j   l f i s
                                         e               p                e   f n t
                                         I               I                I   w a 4 Y
                                                                              a   I I
                                                                          I I
1081     AGCTTTTTAATTTGTAAAGGGGTTAATAAGGAATATTTGATGTATAGTGCCTTGACTAGA  1140
         ----+----+----+----+----+----+----+----+----+----+----+----+
         TCGAAAATTAAACATTTCCCCAATTATTCCTTATAAACTACATATCACGGAACTGATCT
```

FIG.9K

```
             S                              C         E                         N    B
             a                              j         c     S                   l    sM
             uD           M                 e         o     c         M         a    as
             3p           n                 I         R     r         s         I    Be
             An           l                 I         I     F         e         I    II
             II           I                             I   I           I     I    /
        GATCCATTTTCTGTTATTGAGGAAAGTTTGCCAGGTGGGTAAAGGAGCATGATTTAAT
 1141   ------+---------+---------+---------+---------+---------+ 1200
        CTAGGTAAAAGACAATAACTCCTTTCAAACGGTCCACCCAATTTCCTCGTACTAAATTA

H      M
                                              i      a
                          M       E    c       n     C     c
                          b       c    o       d     A  e  v   i
                          o       o    R       I     v  I  i   R
                          I       R    I       I     I  I  R   I
                          I       I    I       I     I  I  I   I
                            I       I    I       I     / 
        CCAGAAGAAGCAGAGGAAAACTAAAACAAGTGTCCTGGAAGCTTGTAACAGAGTATGCAATG
 1201   ------+---------+---------+---------+---------+---------+ 1260
        GGTCTTCTTCGTCTCCTTTTGATTTTGTTCACAGGACCTTCGAACATTGTCTCATACGTTAC
```

FIG.9L

```
         T
         t
         h
      B  1   B
      s  1   s
      r  I   b                                          T
      D  I   I                                          s
      I                                           R     p  R
                                                  s     A5F  s
                                                  a     p0o  a
                                                  I     o9k  I
                                                        III
                                                        /
      GAAACAAAAATGTGATGATGTGTTGTTATTGCTTGGGATGTACTTGGAATTTCAGTACAGT
1261  -----+----+----+----+----+----+----+----+----+----+----+----+ 1320
      CTTTGTTTTACACTACTACACAACAATAACGAACCCTACATGAACCTTAAAGTCATGTCA

N
                                                         l
                                                         a
                                                   R     I
                                                   s     I
                      M   C                  C     a     I
                      D   v                  v     I
         M   C        s   i                  i
         s   j        e   j   R              J
         e   e        I   I   s              I
         I   I            /   a
                          1   I
      TTTGAAATGTGTTAAAAATGTATTAAAAAAGAACAGCCCAGCCACTATAAGTACCATGAA
1321  -----+----+----+----+----+----+----+----+----+----+----+----+ 1380
      AAACTTTACACAAATTTTACATAATTTTTCTTGTCGGGTCGGTGATATTCATGGTACTT
```

FIG.9M

```
          C          AB
       C  v          Mps T            N
       B  i       C  wao  M           d
       j  R       v  oBF  w           e
       e  I       J  eee  o           I
       I  I       I  III  I           I
                  //
      AAGCATTTATGCAAATGCTGCTATATTTGCTGACAGCAAAAAACCAAAAACCATATGCCAA
1381  ------+---------+---------+---------+---------+---------+ 1440
      TTCGTAATACGTTTACGACGATATAAACGACTGTCGTTTTTGGTTTTTGGTATACGGTT C                                                 T
          AvF       C                                       s
       C  lia       v              C                        p     M  B
       v  uJu       i              v     A                  5     s  f
       J  III       J              J     c                  0     e  a
       I  III       I              I     i                  9     I  I
          //
      CAGGCTGTGTTGATACTGTTTTAGCTAAAAAGCGGGTTGATAGCCTACAATTAACTAGAGAA
1441  ------+---------+---------+---------+---------+---------+ 1500
      GTCCGACAACTATGACAAAATCGATTTTTCGCCCAACTATCGGATGTTAATTGATCTCTT
```

FIG.9N

```
                  H              T                      T
                  i              t                      t
                  n              h                      h
                  H   M          l  D                   l
                  s   s          a  u   D               l B
                  c   e          l  3   p   A           l c
                  p   I          I  I   I   I           I I
                  I   I                                 I I
1501  CAAATGTTAACAACAGATTTAATGATCTTTTGGATAGGATGGATATAATGTTTGGTTCT  1560
      --------+---------+---------+---------+---------+---------+
      GTTTACAATTGTTGTCTAAATTACTAGAAAACCTATCCTACCTATATTACAAACCAAGA

D  F S
                                                        r  o f
                                                        d  k c
                                                        I  I I

T            C
                                t            t
                                h            h
                  C  A          l  M      B  l  V
                  v  l          C  b      l  i  J
                  i  w          M  l      o  l  I
                  J  N          I  I      k  I  I
                  I  I          I  I      I     I
1561  ACAGGCTCTCGCTGACATAGAAGAATGGATGGCTGGAGTTGCTTGGCTACACTGTTTGTTG  1620
      --------+---------+---------+---------+---------+---------+
      TGTCCGAGACGACTGTATCTTCTTACCTACCGACCTCAAGACCGAACGATGTGACAAACAAC

```
                        H                              MD              C        N
                        i T                            s r             v N      C 1 B
                        n f                            e a             i s      v N a s R
                        f i                            I I             R i      i s l r s
                        I I                            I I             I I      R i I G a
                        / /                                                     I I I I I
      CCCAAAAATGGATTCAGTGGTGTATGACTTTTTAAAAATGCATGGTGTGTACAACATTCCTAAA
1621  ------+---------+---------+---------+---------+---------+  1680
      GGGTTTTACCTAAGTCACCACATACTGAAAAATTTTACGTACCACATGTTGTAAGGATTT

S         T
                              A a       s
                    C         a 9       p                         T
                    v B  M D  v u  M 5                            t
                    i s  s r  a 9  u 0                            h       M
                    J r  e a  I 6  n 9                      B     1 B     B C s P
                    I I  I I  I I  I I                      b     o s T A s v p v T
                    / /       / /                           v     l o s l o i A u s
                                                            I     I F e u F J l i e
                                                                  I I I I I I I I
                                                                  /  ///
      AAAAGATACTGGCTGTTTAAAGGACCAATTGATAGTGGTAAAACTACATTAGCAGCTGCT
1681  ------+---------+---------+---------+---------+---------+  1740
      TTTTCTATGACCGACAAATTTCCTGGTTAACTATCACCATTTTGATGTAATCGTCGACGA
```

TTGCTTGAATTATGTGGGGGAAAGCTTTAAATGTTAATTTGCCCTTGGACAGGCTGAAC
1741  ------+---------+---------+---------+---------+---------+ 1800
      AACGAACTTAATACACCCCCTTTCGAAATTACAATTAAACGGAACCTGTCCGACTTG

C                                                              B
                Av                                                             s
                li               B                          M                  p   MB 2F
                uJ               s                          n                  l   nm 80
            C   II               r                          l                      lg 6k
            ABv  /               I                          I                  /   II II
            lfi                                                                       /
            uaJ
            III
             /

TTTGAGCTAGGAGTAGCTATTGACCAGTTTTTAGTAGTTTTTGAGGATGTAAAGGGCACT
1801  ------+---------+---------+---------+---------+---------+ 1860
      AAACTCGATCCTCATCGATAACTGGTCAAAAATCATCAAAAACTCCTACATTTCCCGTGA
```

FIG.9R

```
                                E              N                              C C
                                BcS     MT     l                              S v aP
                          S     socH    as     a  R                           f i cS
                          s     aRrp    ep     I  s                           c R 8t
                          p     JIFh    I4     I  a                           I I II
                          I     IIII    I5     I  I                           I I II
                                  /     II          /                           /
      CAAATATTTCCCCTGGAATAGTCACCATGAATGAGTACAGTGTGCCTAAAACACTGCAG
1981  ----+----+----+----+----+----+----+----+----+----+----+----+  2040
      GTTTATAAAGGGGACCTTATCAGTGGTACTTACTCATGTCACACGGATTTTGTGACGTC H                         S  H                  E
           C  a                      aCa           B  c S  c          M
           vHe                       uve        MD sr  o R  r         w
           iaI                       9iI        sr  r R I  F  o
           JeI                       6JI        ea  D I I  I  I
           III                       III        II  I I I  I  I
             //                        /
      GCCAGATTTGTAAAACAAATAGATTTTAGGCCCAAAGATTATTTAAAGCATTGCCTGGAA
2041  ----+----+----+----+----+----+----+----+----+----+----+----+  2100
      CGGTCTAAACATTTTGTTTATCTAAAATCCGGGTTTCTAATAAATTTCGTAACGGACCTT
```

FIG.9S

```
                                    T                     B
                                    s                     s
                                    p                     r
                                    M5                    D
                                    s0                    I
                                    e9
                                    II
2101 CGCAGTGAGTTTTGTTAGAAAAGAGAATAATTCAAAGTGGCATTGCTTTCTTATG 2160
     ----+----|----+----|----+----|----+----|----+----|----+
     GCGTCACTCAAAACAATCTTTTCTCTTATTAAGTTTCACCGTAACGAAAGAATAC

T           C     M              T
     s     R     vD    w              s
     p     s     id    o              p5
     M5    a     Je                   0
     s0    I     II                   9
     e9                                I
     II
2161 TTAATTTGGTACAGACCCTGTGGCTGAGTTTGCTCAAAGTATTCAGAGCAGAATTGTGGAG 2220
     ----+----|----+----|----+----|----+----|----+----|----+----|----+
     AATTAAACCATGTCTGGACACCGACTCAAACGAGTTTCATAAGTCTCGTCTTAACACCTC
```

FIG.9T

```
2221 TGGAAAGAGAGATTGGACAAAGAGTTTAGTTTGTCAGTGTATCAAAAAATGAAGTTTAAT 2280
     ------+---------+---------+---------+---------+---------+
     ACCTTTCTCTCTAACCTGTTTCTCAAATCAAACAGTCACATAGTTTTTACTTCAAATTA
                                                             M
            T                                                s
            s                              c                 e
            p                              vD                I
         C  5                              id
         v  0                              Je
         i  9                              I I
         J  I
         I

2281 GTGGCTATGGGAATTGGAGTTTTAGATTGGCTAAGAAACAGTGATGATGATGAAGAC 2340
     ------+---------+---------+---------+---------+---------+
     CACCGATACCCCTTAACCTCAAAATCTAACCGATTCTTTGTCACTACTACTACTTCTG
```

FIG.9U

```
          E
         Ccs  M                                                               N
         Bvoc b                                      B                        1    MH
         biRr  o                                     c                        Pa   biDB
         sJIF  I                                M    c                        ll   ionDb
         IIII  I                                b    I                        eI   Ifes
         ///                                    o    I                        II   IIII
                                                I
2341 AGCCAGGAAAATGCTGATAAAAATGAAGATGGTGGGAGAAGAACATGGAAGACTCAGGG 2400
     ----+----+----+----+----+----+----+----+----+----+----+----+
     TCGGTCCTTTTACGACTATTTTACTTCTACCACCCCTCTTGTACCTTCTGAGTCCC H  H                  B   C                  E
            N       iT i                  sS  v                  c
            1    B  nf n                  at  i                  o  H  S
            M    s  fi 4                  Jy  J                  OCaNa      M
            b    m  II I                  II  I                  lveluD     n
            o    F                        II                     0iIa9d     1
            I    I                        /                      9JII6e     I
            I                                                    IIIVII
                                                                  ///
2401 CATGAAACAGGCATTGATTCACAGTCCCAAGGCTCCATTCAGCCCCTCAGTCCTCACAG 2460
     ----+----+----+----+----+----+----+----+----+----+----+----+
     GTACTTTGTCCGTAACTAAGTGTCAGGGTTCCGAGTAAAGTCCGGGAGTCAGGAGTGTC
```

TCTGTTCATGATCATAATCAGCCATACCACATTTGTAGAGGTTTTACTTGCTTTAAAAAA
2461   ------+---------+---------+---------+---------+---------+  2520
       AGACAAGTACTAGTATTAGTCGGTATGGTGTAAACATCTCCAAAATGAACGAAATTTTT

T
                                                       s          H
                                  R                    C  p       i
                                  M  l                 v  M  B  5 MnH
                                  n  e                 i  u  s  0 scp
                         M        l  A                 R  n  m  9 eIa
                         n        I  I                 I  I  I  I III
                         l
                         I                       STOP"T"  /

CCTCCCCACACCTCCCCCCTGAAACCTGAAACATAAAATGAATGCAATTGTTGTTAACTT
2521   ------+---------+---------+---------+---------+---------+  2580
       GGAGGGTGTGGAGGGGGACTTTGGACTTTGTATTTTACTTACGTTAACAACAATTGAA
```

FIG.9W

```
            C           M                        T
         C  B           a                        s
         v  s  T  a  v  B  e                     p  S
         i  o  s  l  i  b  I                     A  5  f
         R  F  e  u  J  v  I                     p  0  a
         I  I  I  I  I  I  I                     o  9  N
                                                 I  I  I
         \  \  \  \  \  /  /                     \  \  /
      GTTTATTGCAGCTTATAATGGTTACAAATAAAGCAATAGCATCACAAATTCACAAATAA
2581  ----+----+----+----+----+----+----+----+----+----+----+---- 2640
      CAAATAACGTCGAATATTACCAATGTTTATTCGTTATCGTAGTGTTTAAGTGTTTATT

C
               B  v  B
               s  i  f
               I  I  I
               \  /  /                              mR       a

AGCATTTTTTTCACTGCATTCTAGTTGTGGTTTGTCCAAACTCATCAATGTATCTTATCA
2641  ----+----+----+----+----+----+----+----+----+----+----+---- 2700
      TCGTAAAAAAAGTGACGTAAGATCAACACCAAACAGGTTTGAGTAGTTACATAGAATAGT
```

FIG.9X

```
              N             S    E
              1     BB  NaBBc S         C                     M   B  M
              Aa    asDlussoAc          Av          M         n   s  n         M M M
              1I    mtpa3aeR1r          li          n         1   e  1         n n n
              wI    HYnIAJRIwF          uJ          1         I   R  I         1 1 1
              II    IIIVIIIII           II          I             I            I I I
                    ////   /        /
          TGTCTGGATCCCCAGGAAGCTCCTCTGTGTCCTCATAAACCCTAACCTCCTCTACTTGAG
     2701 ----------+---------+---------+---------+---------+---------+ 2760
          ACAGACCTAGGGGTCCTTCGAGGAGACACAGGAGTATTTGGGATTGGAGGAGATGAACTC T
                    B                                                       s          M T
                    c       CB           B                             C    p     M    a s
                    C  jf   CBe    vsT   B                             Mj   CM5   M    e p
                    b  eo   js8    ios   c                             ne   js0   n    I 4
                    v  Pk   e13    JFe   c                             1P   ee9   1    I 5
                    I  II   III    III   I                             II   III   I    I I
                                                                                       /
          AGGACATTCCAATCATAGGCTGCCATTCCACCCCTCTGTGTCCTCCTGTTAATTAGGTCAC
     2761 ----------+---------+---------+---------+---------+---------+ 2820
          TCCTGTAAGGTTAGTATCCGACGGTAAGGTGGGAGACACAGGAGGACAATTAATCCAGTG
```

FIG.9Z

```
              H           C       C   C   C         E      B
              i           A       A   v   j         c      s
              n           v       v   i   e        oS     p    H S
              c           l       l   R   P        Oa  C Bl CaNa
              I       R   I       I   I   I        1uBvAa2Bjelu
              I       1           C                09mipn8seIa9
                      e   A       A                96gJaI6bPII6
                      A   v       v                IIIIIIIIIVI
                      I   I       I                / / / /   ///
                                           C
                                           v   M
                                           i   n
                                           R   l
                                           I   I 2941 TGTCAACACAGCAGAAACATACAAGCTGTCAGCTTTGCACAAGGGCCCAACACCCTGCTCAT 3000
     ACAGTTGTCGTCTTTGTATGTTCGACAGTCGAAACGTGTTCCCGGGTTGTGGGACGAGTA 3001 CAAGAAGCACTGTGGTTGCTGTGTGTTAGTAATGTGCAAAACAGGAGGCACATTTTCCCCAC 3060
     GTTCTTCGTGACACCAACGACACAATCATTACACGTTTGTCCTCCGTGTAAAAGGGGTG
```

FIG.9A'

```
             H     N                    B              S
             i     l                    f              a     N
             g     a                    a              u  D  l  X
             E     I                    I              3  p  a  c
             I     V                    I              A  n  w  m
             I     I                    I              I  I  I  I
      CTGTGTAGGTTCCAAAATATCTAGTGTTTTCATTTTTACTTGGATCAGGAACCCAGCACT
3061  ------+---------+---------+---------+---------+---------+ 3120
      GACACATCCAAGGTTTTATAGATCACAAAAGTAAAAATGAACCTAGTCCTTGGGTCGTGA

B              C
                         s              v
                         r              i
                         I              J
                                        I
      CCACTGGATAAGCATTATCCCTTATCCAAAAACAGCCTTGTGGTCAGTGTTCATCTGCTGAC
3121  ------+---------+---------+---------+---------+---------+ 3180
      GGTGACCTATTCGTAATAGGGAATAGGTTTTGTCGGAACACCAGTCACAAGTAGACGACTG
```

FIG.9B'

```
          H           M              H  S
          i           a              i  Aa
          n  S        e              n  vu  S    f
          c  f        I              4  a9  I6   c
          I  c        I              I  I   I    I
          I  I        I
        TGTCAACTGTAGCATTTTTTGGGGTTACAGTTTGAGCAGGATATTTGGTCCTGTAGTTTG
3181    ---------+---------+---------+---------+---------+---------+ 3240
        ACAGTTGACATCGTAAAAAACCCCAATGTCAAACTCGTCCTATAAACCAGGACATCAAAC

A                             T
                      cN                            s
                 CB   C                             p
                 S vsPAvt   Bel                     A5
                 f ioslis   bIa                     p0
                 c RFtuJe   vII                     o9
                 I IIIIII   IIV                     II
                   //       /                       /
        CTAACACACCCTGCAGCTCCCAAAGGTTCCCCACCAACAGCAAAAAAATGAAAATTGACC
3241    ---------+---------+---------+---------+---------+---------+ 3300
        GATTGTGTGGGACGTCGAGGGTTTCCAAGGGGTGGTTGTCGTTTTTTACTTTTAAACTGG
```

FIG.9C'

```
                      B             N            C
                      MsR           l            v B    M
                      smc           a            i s    s
      BB              1Fa           I            R m    e
      ss              III           I            I I    I
      11               /                          /
      II
      CTTGAATGGGTTTTCCAGCACCATTTTCATGAGTTTTTTGTGTCCCTGAATGCAAGTTTA
3301  ------+---------+---------+---------+---------+---------+ 3360
      GAACTTACCCCAAAAGGTCGTGGTAAAAGTACTCAAAAAACACAGGGACTTACGTTCAAAT M                                          C
      a              D    M M   M   M e          Av      S
      e              d    s n   a   l I          li      s
      I              e    e l   e   I I          uJ      p
      I              I    I I   I   I I          II      I ACATAGCAGTTACCCCCAATAACCTCAGTTTTAACAGTAACAGCTTCCCACATCAAAATAT
3361  ------+---------+---------+---------+---------+---------+ 3420
      TGTATCGTCAATGGGGGTTATTGGAGTCAAAATTGTCATTGTCGAAGGGTGTAGTTTTATA
```

FIG.9D'

```
                                        T
                                        s                T
                                        p                s
          R                              MDS5M           Ep           C
          l           M                 srw0n           Ac5    B      v      S
          e           s                 eaa91           po0    f      i      f
          A           e                 IIIII           oR9    a      J      c
          I           I                   //            III    I      I      I 3421  TTCCACAGGTTAAGTCCTCTCATTTAAATTAGGCAAAGGAATTCTAGCCACACTGTAGCAAG  3480
      ----+----+----+----+----+----+----+----+----+----+----+----+
      AAGGTGTCCAATTCAGGAGTAAATTTAATCCGTTTCCTTAAGATCGGTGTGACATCGTTC B
                                                              p    H
          H                                                   Mu   i
          i           P      B      B                         BCsl nP  C    A     f
          n           l      b      p                         Asvp1DdvAvt   f     l
          f           e      v      m                         loiA0dIulis   l     I     I
          I           I      I      I                         uFJ12eIIuJe   I     I     I
                                                              IIIIIIIIII
                                                                 //   //

3481  GCAGTTGTTCTTTGTCTCTGGAGAGTCATCTGTAAACTGTTTTTCAGCTGCTAAGCTTTTAC  3540
      ----+----+----+----+----+----+----+----+----+----+----+----+
      CGTCAACAAGAAACAGAGACCTCTCAGTAGACATTTGACAAAAAGTCGACGATTCGAAAATG
```

FIG.9E'

```
        C                               B
        v                               s                      M   B         M D
     M  i                               a            M         n   s         D M
     s  j                               B            n   B     l   l         s s
     e  J                               I            l   I     I   I         e e
     I  I                                             I                      l l
                                                                             I I
      TTAAGCCTTTTTGATGTTCATCAGGATTGCCCATTTGAGGATTAAAAAGCACTCCACCT
3541  ------+---------+---------+---------+---------+---------+  3600
      AATTCGGAAAAACTACAAGTAGTCCTAACGGGTAAACTCCTAAATTTTCGTGAGGTGGA

C                                                         B
       A v M  A                                                     s
       l i n  c               B    M                       C        p   C  M
       u J l  c               s    s                       C j      2   j  n
       I I I  I               r    e                       j e      4   e  l
          I                   I    I                       e P      I   I  I
                                                           I I
                                                             /
      CAGTGAAGCTGTCTACTCCAGTTTTAACTTCTAGAACTTCTATTCCTCCTTTTATGACGA
3601  ------+---------+---------+---------+---------+---------+  3660
      GTCACTTCGACAGATGAGGTCAAAATTGAAGATCTTGAAGATAAGGAGGAAAATACTGCT
```

FIG.9F'

```
        C              B         A                          E
       Av            C C       s DN        c              BC  BcS   B
       li            vCj     pBrl        eBC            AsvT soc   s
       uJ           ije     2sda        Ibj            lois aRr   p
       II           ReP     4rII        Ive            uFJe JIF   G
                    III     IIIV        III            IIII III   I
                     /       //          /              //  /
       GCTTTGGCACTTGCACTGGTTCCTTTGGTTTTTGGGAGCTGCCCCTGGACAACTTCCTT
3661   ------+---------+---------+---------+---------+---------+   3720
       CGAAACCGTGAACGTGACCAAGGAAACCAAAAAACCCTCGACGGGACCTGTTGAAGGAA S   H                                      M
               M aNCa       H                               a
               b ulveB      i              M                e      R    C
               o 9aiIc      n   C          w                I      s    v
               I 6IJIc      d Av           o                I      a    i
               I IVIII      I li           I                I      I    J
                            I uJ                                        I
                            I II
                             /
       TTCTTTTTTGTGTGGGCCATCTTCTTCATAAGCTTTTAGAGCAGAAGTAACACTTCCGTACAGG
3721   ------+---------+---------+---------+---------+---------+   3780
       AAGAAAAAACACCCGGTAGAAGTATTCGAAAATCTCGTCTTCATTGTGAAGGCATGTCC
```

FIG.9G'

```
                                              B    C      E
                             M    D           s    v      c   s    N C
         H                   n    d           e    i      o   c    l v
         a                   l    e           R    R      R   r    a i
         HBeFS               I    I           I    I      I   F    I J
         afIot                                                I    I
         eaIku                                                I    V I
         IIIII
         / / /
         CCTAGAAGTAAAGGCAACACATCCACTGAGGAGCAGTTCTTTGATTTGCACCACCAGGAGCC
3781     ---------+---------+---------+---------+---------+---------+ 3840
         GGATCTTCATTTCCGTTGTAGGTGACTCCTCGTCAAGAAACTAAACGTGGTGGTCCTCGG

T                                          C
         s                                          v          C
         p      T                                   i          A v
         A5     s                                   R          v i
         p0     p                         C         I          i l
         o9     A5  M  H B                v                    J u
         I I    p0  n  p s                i                    I J
         / /    o9  l  h g                R                    I I
                I I I  I I                I                    /
         TCAAATTTTTCAATAAATTCACCTGACTGCACATTAGGACTTTGGCTTTGAGCTTCCCAC
3841     ---------+---------+---------+---------+---------+---------+ 3900
         AGTTTAAAAAGTTATTTAAGTGGACTGACGTGTAATCCTGAAACCGAAACTCGAAGGGTG
```

FIG.9H'

```
                      Mae                                      S             M    B        B
                      Ddel                                     sp            sm    2        sp
                      deIII                                    pI            lg    86       lI
                      eIII                                     I             I     II       I
      3901 CTCTCAGTTACTTGCTGTGAATACTGTCTGCTTCATCAATATTATCATAGGTGTGCCCAAAT + 3960
           GAGAGTCAATGAACGACTTATGACAGACGAAGTAGTTATAATAGTATCCACACGGGTTTA C       C    B                         H
                v       v H  s       B            C    aB      B
                i       i p  m       s            v HesS       s  a
                R       J h  A       I            i aImt       X I
                I       I I  I       I            J eIAu       I
                                                  I IIII       /
      3961 GATATTTGCAACCCCTTCCCTGTGTTGGCTACTTGTCTCTCCACCATTGTAGGCCTAATGGGAGAC + 4020
           CTATAAACGTTGGGAAGGGACAACCGATGAACAGAGTGGTAACATCCGGATTACCCTCTG
```

FIG.9T

```
             Hin                              Tsp                              Tsp
             4                                509                              509
             I                                I    Mse  Cj  M5V
                                                   I    PI  sOs
                                                        I   e9p
                                                            III/

4021 AAAGTAGAGTAGTAATCTTGTAAAGAGTTATACCAATTAACAGGAGCATTAATTACTGTC 4080
     TTTCATCTCATCATTAGAACATTTCTCAATATGGTTAATTGTCCTCGTAATTAATGACAG

BcI                          MseI
                 sjM                          sb
                 mne                          eo
                 FPI                          II
                 III                          I 4081 CAAGTAGTTTCCTCTAAAAACCTTGCCAAACTGTCCCTTAAATATCTTTGGGTTCTTCTT 4140
     GTTCATCAAAGGAGATTTTTGGAACGGTTTGACAGGGAATTTATAGAAACCCAAGAAGAA
```

FIG.9J'

```
                               C                    CA B                                  H
                               AvM                  vvBsS           H                     i
                               lin                  irfat           p                     n     C
                               uJl                  JIaJy           h                     d     Av    M
                               III                  IIIII           I                     I     li    m     e
                                //                   //                                   I     uJ    I     I
                                                                                          I     II    I     I
                                                                                           /     /
       TCAAGCTCCTGTGAGGTGAGCCTAGGAATGTCATTTTGTATTACACGCCAAAAAGCTTGA
4141   ------+---------+---------+---------+---------+---------+ 4200
       AGTTCGAGGACACTCCACTCGGATCCTTACAGTAAAACATAATGTGCGGTTTTCGAACT B           S                   P
                          c           AaN        D        Bf
                  M       e    B      vul        r        sl                              B
                  s       8    s      a9a        d        lM                              p
                  e       3    b      l6l        I        II                              m     l
                  I       I    I      III                 //                              I     I
                                                                                           /

GAAATGGCATTAAAAAGTGTTGGACCCCAATGTCTCGGGGTCAAGATACTGAACACTGTGA
4201   ------+---------+---------+---------+---------+---------+ 4260
       CTTTACCGTAATTTTTCACAACCTGGGGTTACAGAGCCCCAGTTCTATGACTTGTGACACT
```

FIG.9L'

```
                                                    E                    BMT                         C
                                                    c                    cas              C          C      BC
                                                    o                    Beep         B   v          c  Asv
                                              C     4 H                  s8I4     B   b   i   R      c  j loi
                                              j     7Ha                  r3I5     b   v   R   R      j  e uFJ
                                              e     Ihe                  IIII     v   I   I   I      e  I III
                                              I     IaI                                                             4440
                                                    III
      AAAAATCTATACCCCACTTGAGCAACAGCGCTCACACCAGTCACAGTTTGCAGTAAAGCT
4381 -----+---------+---------+---------+---------+---------+----
      TTTTTAGATATGGGGTGAACTCGTTGTGCGAGTGTGGTCAGTGTCAAACGTCATTTCGA
                             /                      /            /

B
                                              s
                     C           B            p        E                           H
             C       AvS         MsT    NC B  l        c                     C  a
             M   w   lif         wos    M lv  aB2      o                     v  HeSM
      vT     w   o   uJc         oFe    w ai  nb8      R                     i  aItn
      is     I   I   III         III    o IJ  Iv6      V                     J  eIul
      Re             ///                I VI  III                               IIII              4500
      II                                       /                                 ///
      GCAAATCCAGCTATAGCAGCAGGAGCCCCAGATATCACAGCATAGGCCTGTGGAGTGAGG
4441 -----+---------+---------+---------+---------+---------+----
      CGTTTAGGTCGATATCGTCGTCCTCGGGGTCTATAGTGTCGTATCCGGACACCTCACTCC
```

```
         B    B   B    C         B        B    B
         s T  s TMs TAv B        B  s B   T    s                            B         B    B
         o s  o s wo s l i b     b  b  mb  s    c    o   PS                 s T       o s  s D
         F e  F e o F e u J v    v  F  v     A O N s a                 M    s    o    F e  J a
         I I  I I I I I I I I    I  I  I    v I l p u                  s    e    F e  I I  I I
          \    \  /  /   /                  a 0 a 5 9                  I
                                              I 9 I I 6
                                            I I I V I I
                                             /  /    /

GCAGCAGCAGCTTCAGACACAGTAGCAATTAGGTCCCCAACAGTGTTAAAGCAGCACCC
4621   ------+---------+---------+---------+---------+---------+   4680
       CGTCGTCGTCGAAGTCTGTGTCATCGTTAATCCAGGGGTTGTCACAATTTCGTCGTGGG

H
                                             i
                       T                B    M n H
         N S           a                s    s c p
         A l a         q                r    e I a
       N S v B a u     I                I    I I I
       c t a b I 9     I
       o y I v I 6
       I I I I I I
        /  /
       ATGGACCTGAAATAAAAGACTAAAAAGACTAAACTTACCAGTTAACTTTCTGGTTTTCAG
4681   ------+---------+---------+---------+---------+---------+   4740
       TACCTGGACTTTATTTTCTGATTTTTCTGATTTGAATGGTCAATTGAAAGACCAAAAGTC
```

FIG.9P'

```
       P f l l l O 8 I
                                   E H  MT             N            N  H
                                   Cc aS as         BCC g  B       B lc a
                   MM           voHecSep         svaMo HsMT     sDNSavBHe
                   ns           iRaIrtI4         ricsA hows    asctiibaI
                   le           JIeIFuI5         Fj8pI aFoe   JaoyIJveI
                   II           IIIIIII          IIIIV IIII    IIIIIIII
                                 //////  /        ///  //       ///  //
       ACCTACGAACCTTAACGGAGGCCTGGCGTGACAGCCGGCGCAGCACCATGGCCTGAAATA
4861   ------+---------+---------+---------+---------+---------+  4920
       TGGATGCTTGGAATTGCCTCCGGACCGCACTGTCGGCCGCGTCGTGGTACCGGACTTTAT
```

```
                                                                M
                                       N                  D   CsP
                                    B IMKRC  D   AE       r  Avpv
                                    a anpsj  d   cc       d  liAu
         M                          n Ilnae  e   ii       I  uJlI
         n                          I VIIII  I   II       I  IIII
         l                            /                      ///
         I
       ACCTCTGAAAGAGGAACTTGGTTAGGTACCTTTCTGAGGCGGAAAGAACCAGCTGTGGAAT
4921   ------+---------+---------+---------+---------+---------+  4980
       TGGAGACTTTCTCCTTGAACCAATCCATGGAAAGACTCCGCCTTTCTTGGTCGACACCTTA
```

FIG.9Q'

```
              B                           E
              s                           BcS  CN          C
         C    m                           soc  vl          a     C
         j    F                           aRr  ia          c     v    M
         e    I                           JIF  JI          8     i    w
         I                                III  IV          I     R    o
                                            /                    I    I
     GTGTGTCAGTCAGTTAGGGTGTGGAAAGTCCCCAGGCTCCCCAGCAGGCAGAAGTATGCAAAGC
4981 -------+---------+---------+---------+---------+---------+ 5040
     CACACAGTCAGTCAATCCCACACCTTTCAGGGTCCGAGGGGTCGTCCGTCTTCATACGTTTCG T                           E
              s    S                      BcSS                    E
         N    p    f                      soec                    B  cS  CN
    ACC1 a    a                           mRxr                    s  Coc vl   C
    pavaNCNS5 N                           FIAF                    a  jRr ia   a
    aciIsjsp0 I                           IIII                    J  eIF JI   c
    B8RIieph9                               /                     I  III IV   8
    IIIIIIII                                                             /    I
    /  //                                                                 //
     ATGCATCTCAATTAGTCAGCAACCAGGTGTGGAAAGTCCCCAGGCTCCCCAGCAGGCAGA
5041 -------+---------+---------+---------+---------+---------+ 5100
     TACGTAGAGTTAATCAGTCGTTGGTCCACACCTTTCAGGGGTCCGAGGGGTCGTCCGTCT
```

FIG.9R'

```
            C            N
            v          ACC1           T
            i         MpavaNNS        s    SB
            R         waciIssp        p    fs          A  F   F   AE   B
            I         oB8RIiph        5    am          c  o   a   cc   c
                      IIIIIIII        0    NF          i  k   u   ii   c
                       ///            9    II          I  I   I   II   I
                                      I
      5101 AGTATGCAAAGCATGCATCTCAATTAGTCAGCAACCATAGTCCCGCCCCTAACTCCGCCC
           ----+---------+---------+---------+---------+---------+ 5160
           TCATACGTTTCGTACGTAGAGTTAATCAGTCGTTGGTATCAGGGCGGGGATTGAGGCGGG M A   F    AE   B                                           T
           w c   a    cc   s                               N           s  p  5
           o i   u    ii   r                        B      lc          p  5  2
           I I   I    II   I                  AE    sBDNavS   AE        0  2  2
                                              cc    asscIit   cc        9     0
                                              ii    JlaoIJy   ii        I
                                              II    IIIIIII   II
                                                      ///
      5161 ATCCCGCCCCTAACTCCGCCCCAGTTCCGCCCCATTCTCCGCCCCATGCTGACTAATTTTT
           ----+---------+---------+---------+---------+---------+ 5220
           TAGGGCGGGGATTGAGGCGGGGTCAAGGCGGGGTAAGAGGCGGGTACCGACTGATTAAAAA
```

FIG.9S'

```
                    H
         C        CBa
    M    v    M   vse
    n    i    n   iaI
    l    R    l   JJI
    I    I    I   III
                   /
     TTTATTTATGCAGAGGCCGAGGC
5221 ---------+---------+---- 5243
     AAATAAATACGTCTCCGGCTCCG
```

Enzymes that do cut:

| | | | | | |
|---|---|---|---|---|---|
| AccI | AceIII | AciI | AflII | AluI | AlwI | AlwNI | ApaI |
| ApaBI | ApoI | AvaII | AvrII | BamHI | BanI | BanII | BbsI |
| BbvI | BccI | Bce83I | BclI | BfaI | BmgI | BpmI | Bpu1102I |
| BsaBI | BsaJI | BsaXI | BsbI | BscGI | BseRI | BsgI | BslI |
| BsmI | BsmAI | BsmFI | BsoFI | Bsp24I | Bsp1286I | BspGI | BsrI |
| BsrDI | BsrFI | BsrGI | BstXI | BstYI | Cac8I | CjeI | CjePI |
| CviJI | CviRI | DdeI | DpnI | DraI | DrdI | DrdII | DsaI |
| EarI | EciI | Eco47III | Eco57I | EcoNI | Eco0109I | EcoRI | EcoRII |
| EcoRV | FauI | FokI | HaeI | HaeII | HaeIII | HgiEII | HhaI |
| Hin4I | HincII | HindIII | Hinfl | HpaI | HphI | KpnI | MaeIII |
| MboII | MmeI | MnlI | MseI | MslI | MspI | MspAlI | MunI |
| MwoI | NcoI | NdeI | NgoAIV | NlaIII | NlaIV | NsiI | NspI |

FIG.9T'

| | | | | | | | |
|---|---|---|---|---|---|---|---|
| Pfl1108I | PflMI | PleI | Psp5II | PstI | PvuII | RcaI | RleAI |
| RsaI | Sau96I | Sau3AI | ScrFI | SexAI | SfaNI | SfcI | SphI |
| SspI | StuI | StyI | SwaI | TaqI | TaqII | Tfil | TseI |
| Tsp45I | Tsp509I | Tth111I | UbaJI | VspI | XcmI | | |

Enzymes that do not cut:

| | | | | | | | |
|---|---|---|---|---|---|---|---|
| AatII | AflIII | AgeI | Alw21I | Alw44I | AscI | AvaI | BaeI |
| BcefI | BcgI | BcgI | BglI | BglII | BpulOI | BsaI | BsaAI |
| BsaHI | BsaWI | BsiI | BsiEI | BsmBI | BspEI | BspLU11I | BspMI |
| BsrBI | BssHII | Bst1107I | BstEII | Bsu36I | ClaI | DraIII | EaeI |
| EagI | Eam1105I | FseI | FspI | GdiII | HgaI | MaeII | MluI |
| MscI | NarI | NciI | NheI | NotI | NruI | NspV | PacI |
| PmeI | PmlI | PshAI | Psp1406I | PvuI | RsrII | SacI | SacII |
| SalI | SapI | ScaI | SfiI | SgfI | SgrAI | SmaI | SnaBI |
| SpeI | SrfI | Sse8387I | SunI | ThaI | Tth111I | XbaI | XhoI |
| XmnI | | | | | | | |

Size of Plasmid: 9.6 kbp
Size of Insert: 5.2 kbp
Calculated size of Tag: 94K
Contains small tag coding region: (+)

FIG.11B'

```
                                Bsp 106 I  Hind II              Eco0109 I
                Pst I              Cla I      Acc I              Dra II
                    EcoR I   EcoR V Hind III     Sal I  Xho I       Apa I
...GGCTGCAGGAATTCGATATCAAGCTTATCGATACCGTCGACCTCGAGGGGGCCC...
...CCGACGTCCTTAAGCTATAGTTCGAATAGCTATGGCAGCTGGAGCTCCCCCGGG...

3' GCTATGGCAGCTGGAGC 5'    (+)
                              KS Primer         (-)

Kpn I
...GGTACCCCAATTCGCCCTATAGTGAGTCGTATTACAATTCACTGGCCGTCGTTTTACAA 3'
...CCATGGGGTTAAGCGGGATATCACTCAGCATAATGTTAAGTGACCGGCAGCAAAATGTT 5'
   |    ← +1 T7 promoter
  657
                   3' GATATCACTCAGCATAA 5'  3' TGACCGGCAGCAAAATG 5'
                           T7 Primer               M13 -20 Primer
```

TRANSGENIC MOUSE MODEL FOR PROSTATE CANCER

REFERENCE TO RELATED APPLICATION

This application is a continuation-in-part of copending U.S. patent application Ser. No. 08/351,365 filed Dec. 9, 1994.

FIELD OF THE INVENTION

The present invention is concerned with a novel transgenic non-human eukaryotic animal model and in vitro cell lines derived from transgenic animal tissues, which permit 1) development of methodologies for the identification, diagnosis and staging of prostate cancer and resulting metastatic disease and 2) the development and rapid screening of organic and inorganic chemical compounds, agents including radiation, and gene-based therapies for the prevention and treatment of prostate cancer and resulting metastatic disease.

BACKGROUND TO THE INVENTION

Prostate Cancer

Prostate cancer will likely claim the lives of 35,000 men in the United States this year alone and some 200,000 more men will be diagnosed with the disease (Silverger, Boring & Squires, 1990). However, progress toward understanding the biology of prostate cancer and the development of new therapies for this disease has been slowed, in part, by the need for new in vivo model systems that adequately reproduce the spectrum of benign, latent, aggressive and metastatic forms of the human disease.

Prostate cancer is a disease quite unique to man. Although naturally occurring prostatic disease has been reported in some canine (Berry, Coffey, & Ewing, 1984) and rodent (Noble, 1977; Pollard, 1973; Pollard & Luckert, 1987; Shain, McCullough, Nitchuk, & Boesel, 1977; Shain, McCullough, & Segaloff, 1975) species, these animals have not provided the appropriate models to adequately study the molecular mechanisms related to the early development and progression of human prostate cancer. To this end, we initiated a research program to establish a transgenic animal model for prostate cancer using a prostate-specific transgene expression system that has been developed based on the regulatory elements of the rat probasin (rPB) gene.

Probasin Gene

The rPB gene encodes an androgen- and zinc-regulated protein specific to the dorsolateral epithelium (Dodd, Sheppard & Matusik, 1983; Matusik, Kreis, McNicol, Sweetland, Mullin, Fleming, et al., 1986; Sweetland, Sheppard, Dodd & Matusik, 1988). Isolation of the rPB gene has facilitated identification of cis-acting androgen response regions within the 5' flanking region (Rennie, Bruchovsky, Leco, Sheppard, McQueen, cheng, et al., 1993). More recently, the ability of the prostate specific rPB gene promoter to target heterologous genes specifically to the prostate in transgenic mice has been demonstrated (Greenber, DeMayo, Sheppard, Barrios, Lebovitz, Finegold, et al., 1994). In these studies, an expression cassette carrying 426 base pairs (bp) of the rPB gene promoter and 28 bp of 5' untranslated region (5'UT) was found to be sufficient to target expression of a bacterial chloramphenicol acetyl transferase (CAT) reporter gene specifically to the prostatic epithelium. These studies demonstrated that the minimal rat probasin promoter was specifically regulated by androgens in vivo with the ability to target developmentally- and hormonally- regulated expression of a heterologous gene specifically to the prostate in transgenic mice.

The latter studies, showing prostate-specific targeting of heterologous gene expression products is described in the aforementioned U.S. Ser. No. 08/351,365 and published in the corresponding WO 94/03594, the disclosures of which are incorporated herein by reference.

SV40 T Antigen

The SV40 early region-tumor antigens (Tag) have the ability to induce transformation in vivo (Brinstar, Chen, Messing, Van Dyke, Levine, & Palmiter, 1984). The SV40 large T antigen acts as an oncoprotein through interactions with the retinoblastoma(Rb) (DeCaprio, Ludlow, Figge, Shew, Huang, Lee, et al., 1988) and p53 (Lane & Crawford, 1979; Linzer & Levine, 1979) tumor suppressor gene products. The small t antigen interacts with a protein phosphatase (Pallas, Shahrik, Martin, Jaspers, Miller, Brautigan, et al., 1990) presumably to regulate activity of the mitogen activated protein kinase activation pathway and the AP-1transcription factor activity (Frost, Alberts, Sontag, Guan, Mumby, & Feramisco, 1994). The SV40 early region tumor antigens have been used successfully in transgenic mice to induce a transformed state in a variety of systems from pancreas (Hanahan, 1985), mammary gland (Tzeng, Guhl, Graessmann, & Graessmann, 1993), to the ductal epithelium of lung and kidney (Choi, Lee & Ross, 1988) and others (see (Adams & Cory, 1991) for review). Since the loss of wild-type p53 and Rb have been implicated in development and progression of prostate cancer (Bookstein, Rio, Madreperla, Hong, Allred, Grizzle, et al., 1990; Cooke, Quarmby, Mickey, Isaacs, & French, 1988; Isaacs, Carter, & Ewing, 1991; Rubin, Hallahan, Ashman, Brachman, Beckett, Virudachalam, et al., 1991), we hypothesized that directly expressing SV40 tumor antigens in the prostate epithelium of transgenic mice might provide a new mouse model for the development and progression of prostate cancer.

Transgenic Animal Models

Previous efforts to establish experimental animal models of prostate cancer have explored other primate systems (Habenicht, el-Etreby, Lewis, Ghoniem, & Roberts, 1989), or have focussed primarily on the effects of sex hormones that displays a very low frequency of spontaneous prostatic disease. For example, rats treated with sex hormones (Noble, 1977) developed adenocarcinoma of the prostate, as did rats treated with methylnitrosourea (Pollard & Luckert, 1987), testosterone and cyproterone (Pollard, Luckert & Snyder, 1989) or methylnitrosourea, dimethylbenzanthracene, or dimethylaminobiphenyl after sequential treatment with cyproterone acetate and testosterone propionate (Bosland & Prinsen, 1990; Bosland, Prinsen, Dirksen, & Spit, 1990). In addition, prostate tumors arise following cadmium (Waalkes, Rehm, Riggs, Bare, Devor, Poirer, et al., 1988) administration to Wistar[Crl:(WI)BR] rats and estradiol and dimethylaminobiphenyl (Shirai, Fukushima, Ikawa, & Ito, 1986) administration to F344 rats. Unfortunately, these protocols induce highly variable primary tumors and are not amenable to studying the molecular events involved in the progression of latent locally defined disease to adenocarcinoma and metastasis. Similarly, efforts to develop in vitro models for prostate cancer have produced the Dunning (Bogden, Taylor, Moreau, & Coy, 1990) (Cooke, et al., 1988), PC-3 (Rubin, et al., 1991) and PC-82 (van & Schroder, 1988) cell lines that are capable of inducing xenograft tumors. More recently, new LnCaP sublines have been developed that are androgen-independent (Thalman, Anezinis, Chang, Zhau, Kim, Hopwood, et al., 1994). However, these systems do not facilitate characterization of the earliest events in the progression of prostate cancer and established tumor cell lines may have been selected either for a number of genetic alterations not found in the primary tumors or acquired mutations in vitro (Carroll, Voeller, Sugars, & Gelmann, 1993; Rubin, et al., 1991). To this end, in vivo gene transfer studies were pursued recently in an attempt to develop a new generation of prostate cancer research models.

Retrovirus mediated gene transfer has been used to develop a mouse prostate reconstitution model (MPR). In this system, the Ha-ras and c-myc genes are first introduced into the fetal urogenital sinus and a reconstituted organ is then transplanted under the renal capsule of host mice leading to the rapid development of adenocarcinoma (Thompson, Southgate, Kitchener, & Land, 1989). MPR has been used previously to demonstrate that co-operativity between Ha-ras and c-myc leads to the transformation of reconstituted prostates (Thompson, Kadmon, Timme, Merz, Egawa, Krebs, et al., 1991; Thompson, Timme, Kadmon, Park, Egawa, & Yoshida, 1993a; Thompson, Truong, Timme, Kadmon, McCune, Flanders, et al., 1993b; Thompson, et al., 1989), and that dietary fenretinide can reduce the incidence of these tumors (Slawin, Kadmon, Park, Scardino, Anzano, Sporn, et al., 1993). Furthermore, MPR studies have demonstrated that TGFβ1 may be a marker in the progression of prostate disease from benign to malignant status (Thompson, et al., 1993b), and more recently, that p53 inactivation is related to increase tumorigenesis, and metastasis (Timme, Park, Ren, Eastham, Baley, Kadmon, et al., 1994).

Previous attempts by other investigators to establish transgenic targeting systems based on the regulatory elements of cellular or viral genes known to be expressed in the prostate have met only with limited success.

Studies in vivo demonstrate that C3(1) is induced 2-to-4 fold transcriptional by androgens (Parker et al, 1988; Parker and Needham, 1985), causing the authors to suggest post-transcriptional regulation (page and Parker, 1982).

When a fragment of the rat C3(1) gene was fused to a heterologous β-gal reporter gene, the spatial pattern of C3(1)-βgal fusion transgene expression was not found to be uniform (Buttyan & Slawin, 1993). Mice carrying a C3(1)-Tag transgene have recently been generated (Maroulakou, Anver, Garrett, & Green, 1994). In the two lines of C3(1)-Tag mice that have been propagated, the males develop prostatic hyperplasia and adenocarcinoma while the female mice develop mammary carcinoma. In general, the majority of male mice were observed to develop prostate adenocarcinoma by 8 months of age. Interestingly, a number of phenotypic abnormalities were also observed in the founder mice with only two animals surviving longer than 20 weeks. The founders displayed osteosarcomas, proliferative lesions of the thyroid, salivary glands and nasal epithelium as well as an unusual form of chondrodysplasia. Therefore, the C3(1)-Tag construct used in these studies appears to lack regulatory regions required to limit expression exclusively to the prostate. In addition, the C3(1) transgene is responsive to both male and female sex hormones. In another case, mice carrying a truncated mouse mammary tumor virus long terminal repeat (MMTV-LTR)-int-2 cDNA construct were originally reported to exhibit a phenotype consistent with benign prostatic hyperplasia (Muller, Lee, Dickson, Peters, Pattengale, & Leder, 1990; Tutrone, Ball, Ornitz, Leder, & Richie, 1993). However, further histological evaluation has revealed the pathology actually occurs in the ampullary gland (G. Cunha, unpublished observations). When a fragment of the promoter for human prostate specific antigen (PSA) was used to target an activated Ha-ras oncogene to the prostate in transgenic mice, the mice developed salivary gland tumors with no apparent pathology in prostate gland (Schaffner, Barrios, Shaker, Rajagopalan, Huang, Tindall, et al., 1994). It is interesting to note that the promoter for the PSA gene, a member of the kallikrein gene family (Riegman, Vlietstra, van, Romijn, & Trapman, 1989), directed expression in salivary gland in transgenic mice since similar observations were not reported in previous transgenic studies using a kallikrein rKlK1 promoter Tag constructs (Smith, Lechago, Wines, MacDonald, & Hammer, 1992).

SUMMARY OF THE INVENTION

In accordance with one aspect of the invention, there is provided a transgenic non-human eukaryotic animal, specifically a mouse, as well as the descendants and ancestors of such animal, which are animal models of human prostate cancer. Such transgenic animals have genomically integrated therewith a nucleic acid molecule comprising:

a first segment which is a 5' flanking region of the rat probasin gene as shown in FIG. 8, (SEQ ID NO: 1)

a segment which is an oncogene encoding the SV40 early region-tumor antigens (Tag) (SEQ ID NO: 2)

The first and second segments of the nucleic acid molecule are operatively connected to effect oncogene product expression in the prostate of the animal.

The nucleic molecule may cointegrate with a matrix attachment region (MAR) that can increase the chance of expression of a randomly integrated transgene molecule. The level of oncogene expression appears to be related to the time of tumor development. In general, all male mice will, following puberty, display pathology of the prostate gland ranging from prostatic intraepithelial hyperplasia (PIN) to adenocarcinoma, with the likelihood of advanced metastatic disease increasing with the age of the animal and the level of transgene expression.

The transgenic animal may have a disease state caused by expression of said oncogene and comprising prostatic hyperplasia, androgen-responsive tumors and androgen-unresponsive tumors. The oncogene segment may be one encoding the SV40 large T antigen or the SV40 small t antigen.

The present invention also provides immortal cell lines derived from prostate tissue of the transgenic animals with such cell line representing a stage of the progression of prostate cancer.

The ability to induce hyperplasia and adenocarcinoma of the prostate in transgenic mice as a consequence of rPB directed oncogene expression, as described herein, provides distinct advantages over previously described model systems. Since both males and females appear to be fertile, it is not anticipated that a biogenic system will need to be implemented to overcome infertility problems as described previously in transgenic studies using the MMTV-LTR promoter (Ornitz, Moreadith, & Leder, 1991; Tutrone, et al., 1993). In addition, the specificity of the rPB promoter facilitates long term studies and the establishment of immortalized cell lines representing the various stages of progression of prostate cancer by reducing the morbidity and mortality associated with tumor development in other organ sites, such as salivary gland, cartilage and thyroid as reported for transgenic mice carrying a C3(1)-Tag construct (Maroulakou, et al., 1994).

BRIEF DESCRIPTION OF DRAWINGS

The file of this patent application contains at least one drawing executed in color, namely FIGS. 2 to 7. Copies of this patent with color drawing(s) will be provided by the Patent and Trademark Office upon request and payment of the necessary fee.

FIG. 8 shows the PB rat genomic sequence from −426 to +28 bp (SEQ ID NO: 1). The start of transcription is shown as V with the number starting immediately after as +1. All negative numbering is relative to the start site of transcription. Sequences beyond +28 define additional number sequences of the first exon for PB.

DESCRIPTION OF PREFERRED EMBODIMENT

As discussed above and in the prior U.S. patent application and WO 94/03594, the rat probasin (rPB) −426/+28 bp promoter fragment targets prostate specific expression that is androgen regulated. In accordance with the present invention, we have now achieved probasin targeting to the prostate in transgenic animals, namely transgenic mice, of the SV 40 early region-tumor antigens, including the large T antigen, to induce prostatic hyperplasia or cancer in the transgenic mouse. These animal lines also have been successfully bred to pass on the disease to their progeny. We have found that the level of oncogene expression appears to be related to the time of the tumor development. In general, all male mice will, following puberty, display pathology of the prostate gland ranging from prostatic intraepithelial hyperplasia (PIN) to adenocarcinoma, with the likelihood of advanced metastatic disease increasing with the age of the animal and level of transgene expression.

The rPB directed oncogene expression achieved herein, leading to epithelial hyperplasia and adenocarcinoma, enables there to be provided transgenic non-human eukaryotic animal models for human prostate disease and also immortalized cell lines representing various stages of progression of prostate cancer.

The expression of the large T-antigen in the transgenic mice provided herein is accompanied by an increased detection of nuclear p53 protein. In addition, prostatic cancer cells produced in the transgenic mice provided herein have a decreased detectable androgen receptor, which suggests that the tumors have progressed to an androgen independent state as does human prostate cancer, whereby the transgenic mice provided herein may be a model for the progression of cancer from an androgen-dependent to an androgen-independent state.

The development of the transgenic mice herein and the provision of the cell lines from prostatic tissue of such transgenic mice permits the development of methodologies for the identification, diagnosis and staging of prostate cancer and resulting metastatic disease. Further those transgenic mice provide a unique animal model system to study the molecular basis of transformation of normal prostatic cells and the factors influencing the progression of metastatic prostate cancer. In addition, such transgenic mice and cell lines may be used for the screening and development of various chemical compounds, agents including radiation and gene-based therapies on prostate cancer, for the prevention and treatment of prostate cancer.

EXAMPLES

Example 1

Construction of the Transgene

Figure 10:
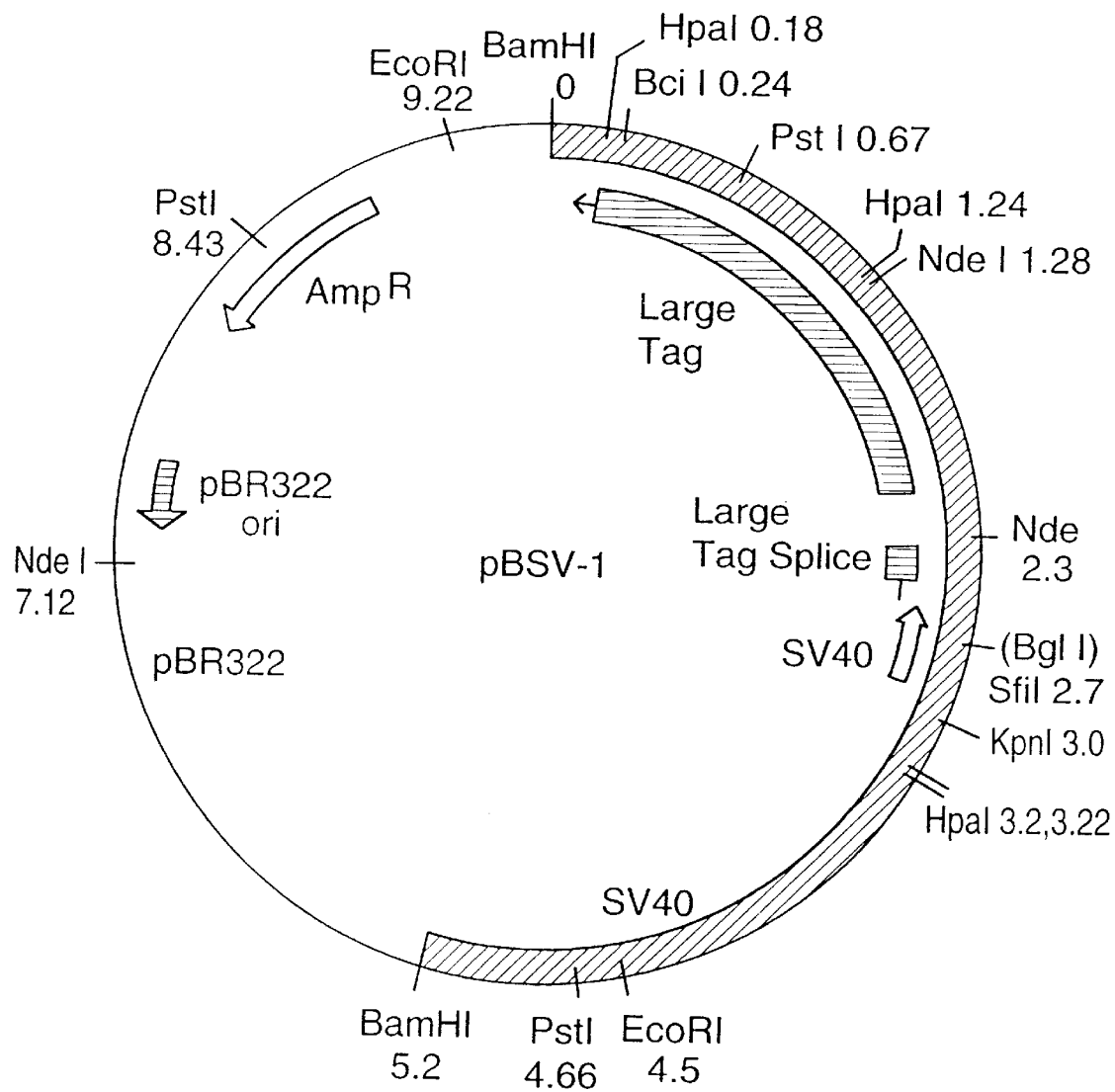
FIG. 10 is a diagrammatic representation of plasmid pBSV-1 containing the SV40 genome showing the restriction sites and location of the large T-antigen encoding element. The plasmid is sized 9.6 kbp with the SV40 insert sized 5.2 kpb. The calculated size of the tag is 94 k.
Figure 11A:
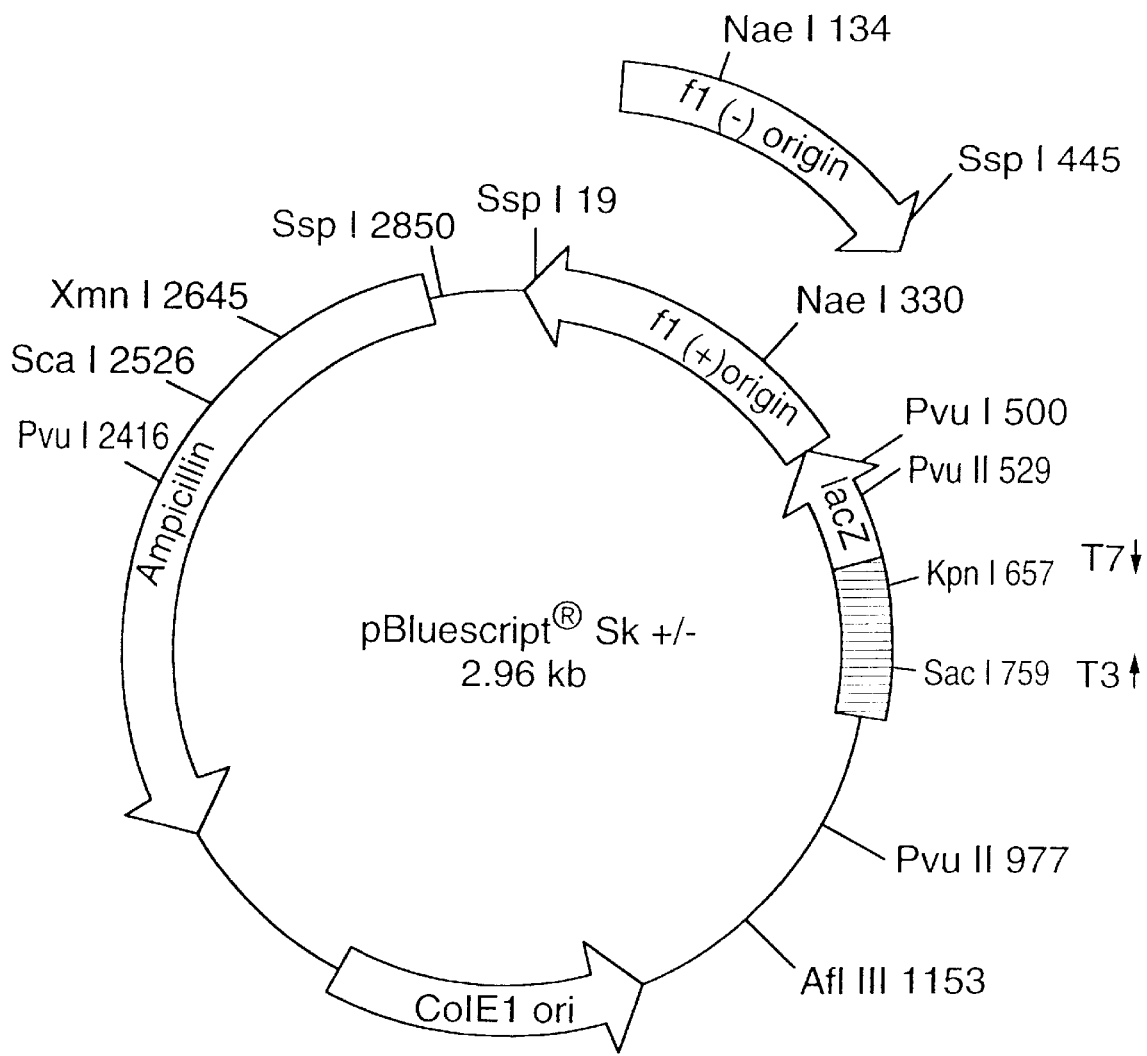
FIG. 11 is a diagrammatic representation of phagemid pBluescript SK +/−, which is a 2958 basepair phagemid derived from pUC19. The SK designation indicates the polylinker is oriented such that lacZ transcription proceeds from Sac I to Kpn I.
Figure 11B:
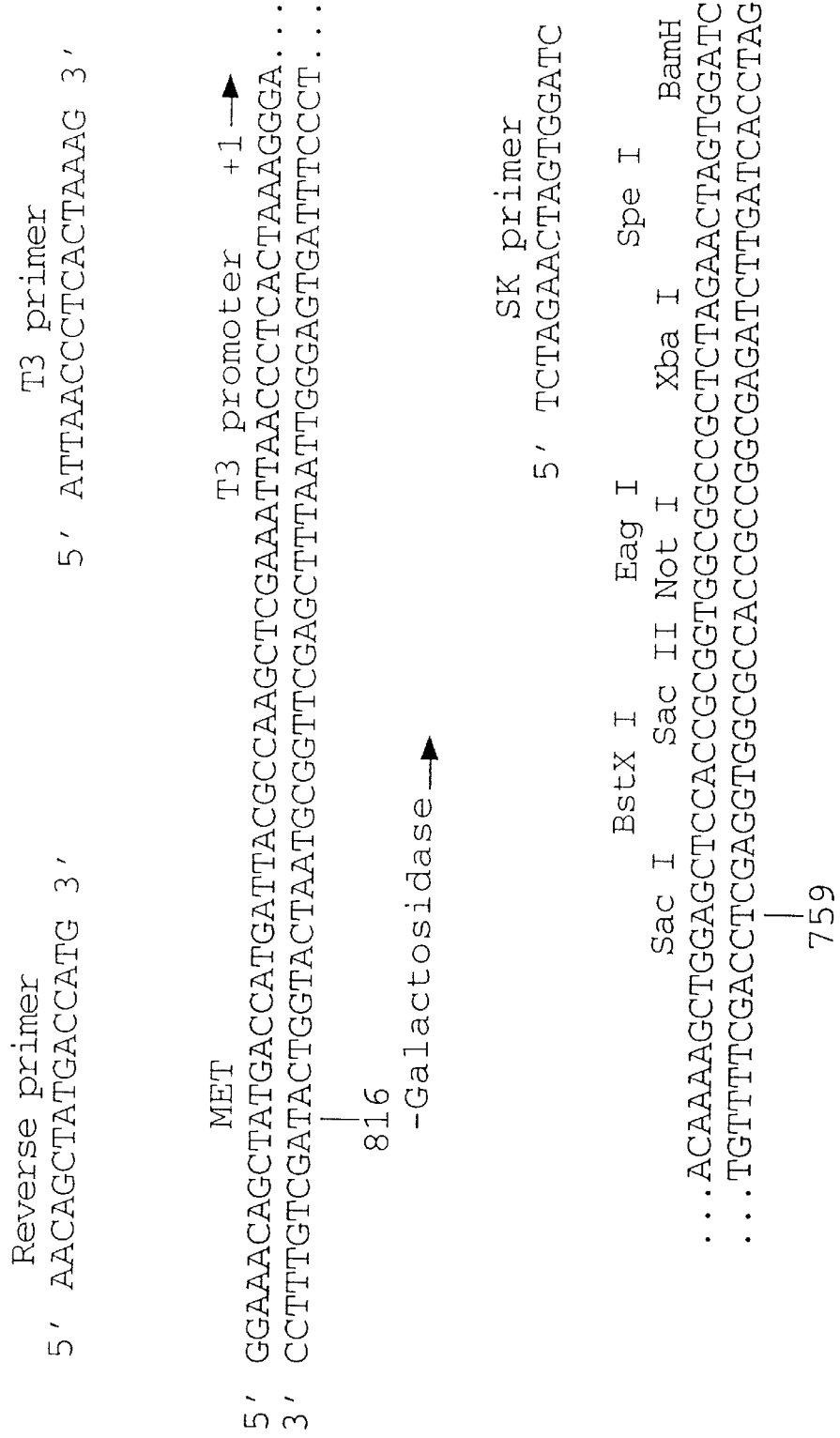

To construct the rat probasin-SV40 T antigen transgene (FIG. 1), the plasmid pBSV-1 (FIG. 10) was digested with BglI, blunt-ended with T4 polymerase, and digested with BamHI to liberate the Tag structural gene. The Tag structural gene was then ligated into pBluescript SK+/- (Stratagene, FIG. 11) carrying the rPB-426/+28 fragment (SEQ ID NO: 1) that had been digested with BamHI and EcoRV, to give the plasmid rPB-Tag. To prepare a linear transgene for microinjection, the plasmid was digested with BssHII, purified by agarose gel electrophoresis and recovered by absorption to Qiagen matrix (Qiaex). The matrix attachment region (MAR) was prepared as described previously (Greenberg, et al., 1994).

Example 2

Production and Screening of Transgenic Mice

Generation of transgenic mice, isolation of mouse tail DNA, and polymerase chain reaction (PCR) based screening assay were as described previously (Greenberg, et al., 1994). The sequences of the synthetic oligonucleotides used in PCR reactions were as follows (5'=3'):
A: CCGGTCGACCGGAAGCTTCCACAAGTGCATTTA (SEQ ID NO: 3)
B. AGGCATTCCACCACTGCTCCCATTCATC (SEQ ID NO: 4)

The architecture of transgene co-integration was analyzed by Southern blotting tail DNA (20 μg) digested with Pst I. Blots were hybridized with ⁻P-labelled Tag-specific probes prepared by the random-oligolabelling method (sp. activity>$10^9$ cpm/μg), washed, and exposed to presensitized XAR5 (Kodak) film.

Example 3

Characterization of Transgenic Mice

Figure 1:
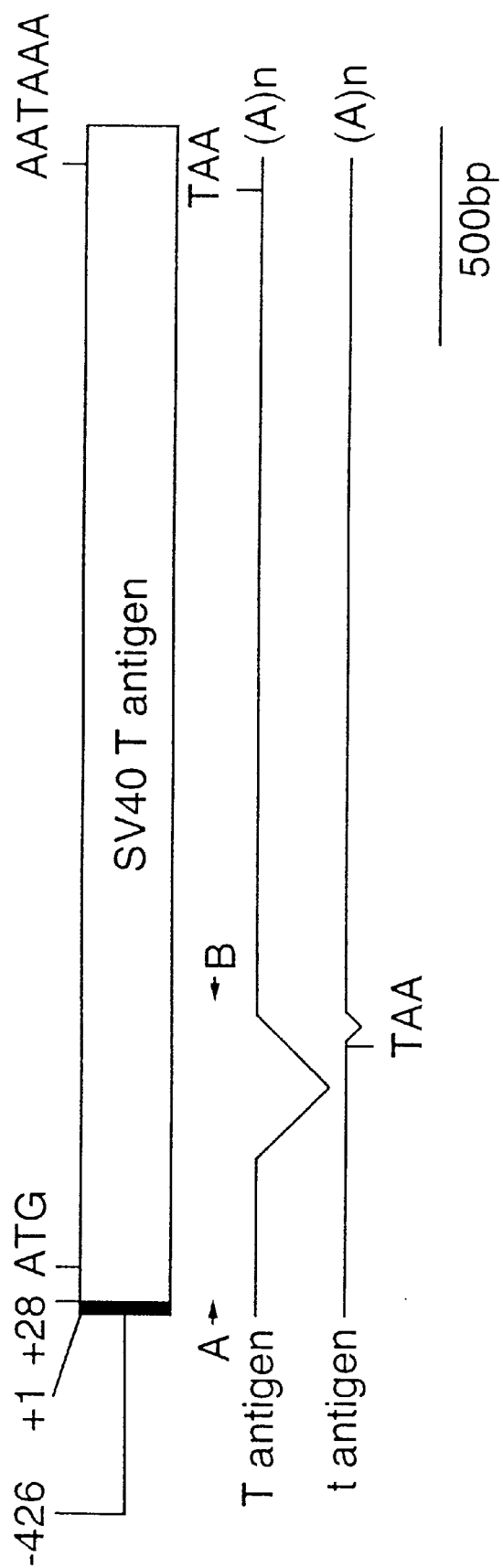
FIG. 1 contains a schematic representation of the PB-Tag transgene. The elements are: −426 to +1, the 5' flanking region of the rat PB gene; +1 to +28, portion of the non-coding first exon of PB (the nucleotide sequence of the −426 to +1 and +1 to +28 elements are shown in the aforementioned U.S. Ser. No. 08/351,365 and WO 94/03594 and FIG. 8); ATG and TAA, delimit the open reading frames; and AATAAA, polyadenylation signals. The alternatively spliced transcripts for T and t antigens are shown. The location and orientation of the primers used for RT-PCR analysis are denoted as A and B.

To determine whether targeted expression of the SV40 T antigen (Tag) would result in transformation of the prostatic glandular epithelium, lines of transgenic mice were generated with a construct carrying the −426/+28 bp PB promoter fragment (SEQ ID NO: 1) fused to the SV40 Tag gene (SEQ ID NO: 2) (FIG. 1). As the upstream matrix attachment region (MAR) of the chicken lysozyme gene has been demonstrated previously to further mediate elevated and tissue-restricted expression of a PB-CAT transgene, lines of PB-Tag mice were also generated by coinjection with the MAR sequence. Mice were generated in both the C57B1/6 and FVB backgrounds as strain specific responses to oncogene mediated transformation of prostate epithelium had been reported previously (Thompson, et al., 1993a).

A total of nine independent founder animals were generated with the PB-Tag construct, of which four carried co-integrated MAR sequences. The founder transgenic mice are identified in the following Table I:

TABLE I

| Construct | FounderID | Sex | Birth Date | Fertile | Express | Time to Tumors |
|---|---|---|---|---|---|---|
| PB-Tag | 5666 | M | 9/27/92 | Yes | Yes | 1 year |
| PB-Tag | 5669 | M | 9/27/92 | Yes | Yes | 1 year |
| PB-Tag | 5672 | M | 9/28/92 | Yes | Yes | ND* |
| PB-Tag | 5679 | F | 9/28/92 | Yes | Yes | 1 year |
| PB-Tag | 7250 | M | 4/12/93 | Yes | Yes | ND |
| PB-Tag/MAR | 8079 | M | 10/2/93 | No | Yes | 10 weeks |
| PB-Tag/MAR | 9244 | F | 11/8/93 | Yes | No | ND |
| PB-Tag/MAR | 8247 | M | 11/8/93 | Yes | Yes | 20 weeks |
| PB-Tag/MAR | 8549B | M | 2/7/94 | ND | ND | ND |

*ND Not Determined

All PB-Tag founder animals successfully passed the transgene on to progeny, with exception of one male (ID 8079) that died at 10.2 weeks that upon necropsy was found to have a large prostate tumor. As previously reported for the PB-CAT studies, PB-Tag expression was found not to be copy number dependent.

Figure 2:
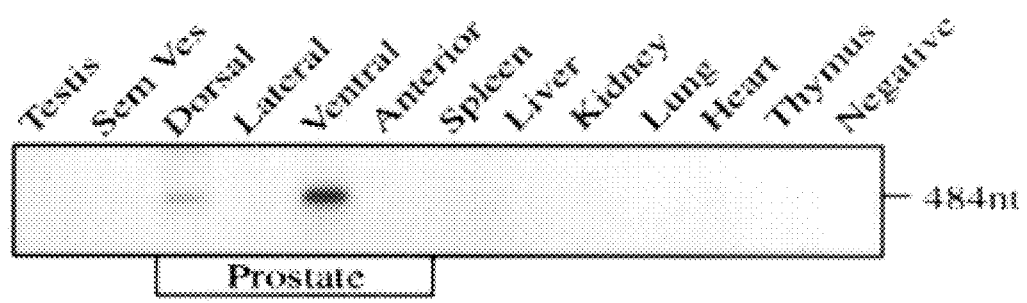
FIG. 2 shows tissue specific expression of PB-Tag in transgenic mice. RNA was analyzed by reverse-transcriptase polymerase chain reaction (RT-PCR). The migration of the 484nut PCR product is shown.
Figure 3:
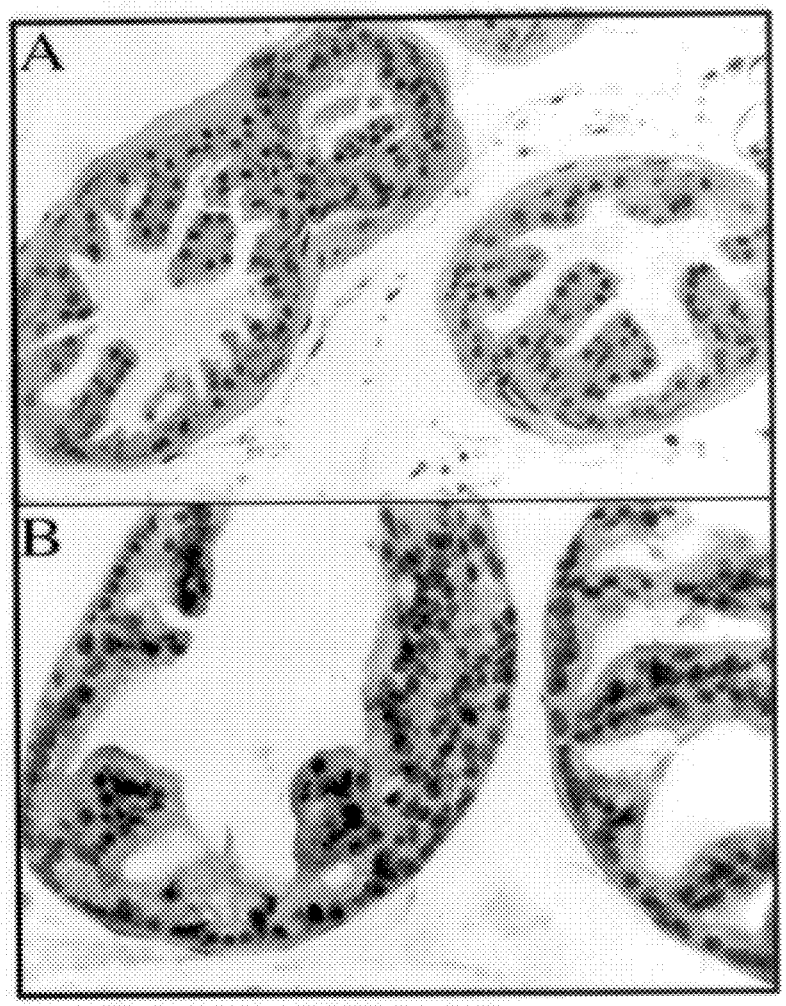
FIG. 3 comprising panels A and B, shows characterization of epithelial hyperplasia in the prostate of a transgenic mouse. Serial paraffin sections were stained with hematoxylin and eosin. A. Prostate of non-transgenic littermate showing typical columnar morphology (200 X). B. Prostate from line 5666 showing polymorphonuclear ductal epithelium and a loss of tall columnar morphology (200 X).

The tissue distribution of prostate-restricted PB-Tag expression in line 5666, as shown in FIG. 2, was found to resemble that determined previously in mice carrying a PB-CAT fusion construct (Greenberg, et al., 1994) with transgene expression restricted to the prostate. The highest levels of transgene expression were detected in the ventral and dorsal lobes of the prostate in sexually mature males. Similar patterns of expression were observed for all lines examined. Histological evaluation of the male accessory glands of line 5666 revealed a profound epithelial hyperplasia in the ventral prostate by 33 weeks of age characterized by excessive and somewhat disorganized ductal epithelium that had diminished cytoplasm (FIG. 3B) in contrast to the tall columnar epithelium observed in the controls (FIG. 3A). As determined by immunohistochemical staining for Tag expression, the absolute level of transgene expression in line 5666 epithelium was low.

Figure 4:
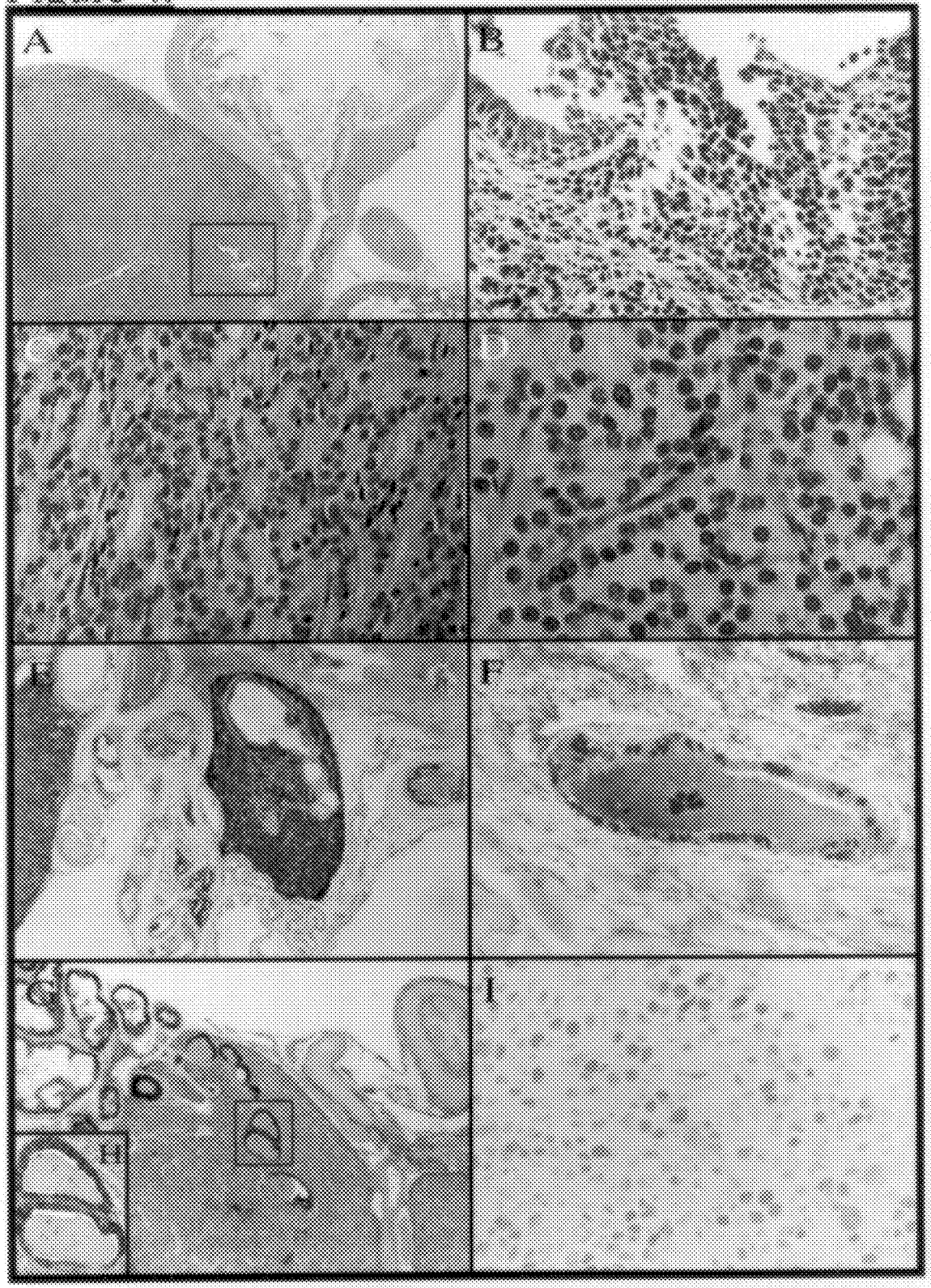
FIG. 4 comprising panels A to I, contains histological analysis of prostate tumors in PB-Tag mice. Paraffin sections were stained with hematoxylin and eosin unless otherwise noted. A. Section through mouse prostate shows poorly differentiated tumor surrounding the urethra (20 X). B. Higher magnification of section shown in (A) demonstrating the hyperchromatic and angular nuclei and small amounts of eosinophilic cytoplasm (200 X). C. Section through human prostate showing poorly differentiated tumor (250 X). D. Higher magnification of section shown in (C) demonstrating sparse stroma and large, polymorphonuclear epithelium (500 X). E. Immunohistochemical analysis of Tag expression showing poorly differentiated tumor with adjacent well-differentiated prostatic ducts (40 X). Dark regions indicate immunoreactivity. F. Poorly differentiated ducts with secretions and Tag-immunoreactive cells in lumen (40 X). G. Immunocytochemical localization of mouse dorsolateral secreted proteins within well differentiated ducts adjacent to (25 X) and H, within the prostate tumor mass (55 X). I. Immunohistochemical localization of p53 with Ab-CM-5. Brown regions indicate immunoreactivity showing even distribution of p53 (400 X). Counterstain is methyl green.

In contrast, founder mouse 8079 developed a large, multinodular neoplasm infiltrating most portions of the prostate by 10 weeks of age (FIGS. 4A, B). Histologically the tumor resembles advanced stage human prostate cancer (FIGS. 4C, D). The neoplastic cells were relatively small and pleomorphic with very hyperchromatic and often angular or molded nuclei and small amounts of eosinophilic cytoplasm. Mitoses were frequently observed, with cells arrayed in nests separated by delicate stroma. These cells surrounded, sometimes infiltrated and often replaced prostatic glands. One lateral lobe of the prostate was partially uninvolved but had malignant cells infiltrating the subepithelial stroma. Atypical hyperplasia of the epithelium was focally present in non-neoplastic glands.

The neoplasm in mouse 8079 displayed very high levels of Tag protein expression in the nuclei of over 80% of the neoplastic cells as determined by immunohistochemical analysis (FIGS. 4E, F). Positively straining nuclei were plentiful in epithelial cells lining some of the non-tumoral glands and interestingly, most of the Tag positive nuclei were indistinguishable from their unstained neighbours.

To confirm the prostatic origin of the neoplasia, immunohistochemical analysis was performed with an antibody prepared against secretions from mouse dorsolateral prostate (Donjacour, Rosales, Higgins, & Cunha, 1990). This antibody specifically recognizes secretory proteins of differentiated epithelial cells and not other cellular components of the mouse dorsolateral prostate. As shown in FIGS. 4G and 4H, only the ducts adjacent to the large tumor as well as some differentiated epithelial cells within the tumor mass showed high levels of dorsolateral specific proteins. These proteins were not detected in the undifferentiated epithelial cells within the tumor tissue.

It has been demonstrated previously that p53 nuclear accumulation is significantly more common in higher grade human prostate cancer (Aprikian, Sarkis, Fair, Zhang, Fuks, & Cordon-Caro, 1994). Since the SV40 large T antigen is known to bind and stabilize p53 in the nucleus (Levine & Momand, 1990; Levine, Momand, & Finley, 1991; Quartin, Cole, Pipas, & Levine, 1994; Shaulsky, Goldfinger, Tosky, Levine, & Rotter, 1991) it was not unexpected that immunohistochemical analysis demonstrated elevated levels of nuclear p53 protein in the neoplastic cells in mouse 8079 (FIG. 4I). It was interesting, however, to observe that the majority of nuclei exhibiting the strongest p53 staining were larger and more pleomorphic than their non-staining neighbors. There was no p53 immunoreactivity detected in the hyperplastic epithelium of line 5666 or in non-transgenic controls.

Figure 5:
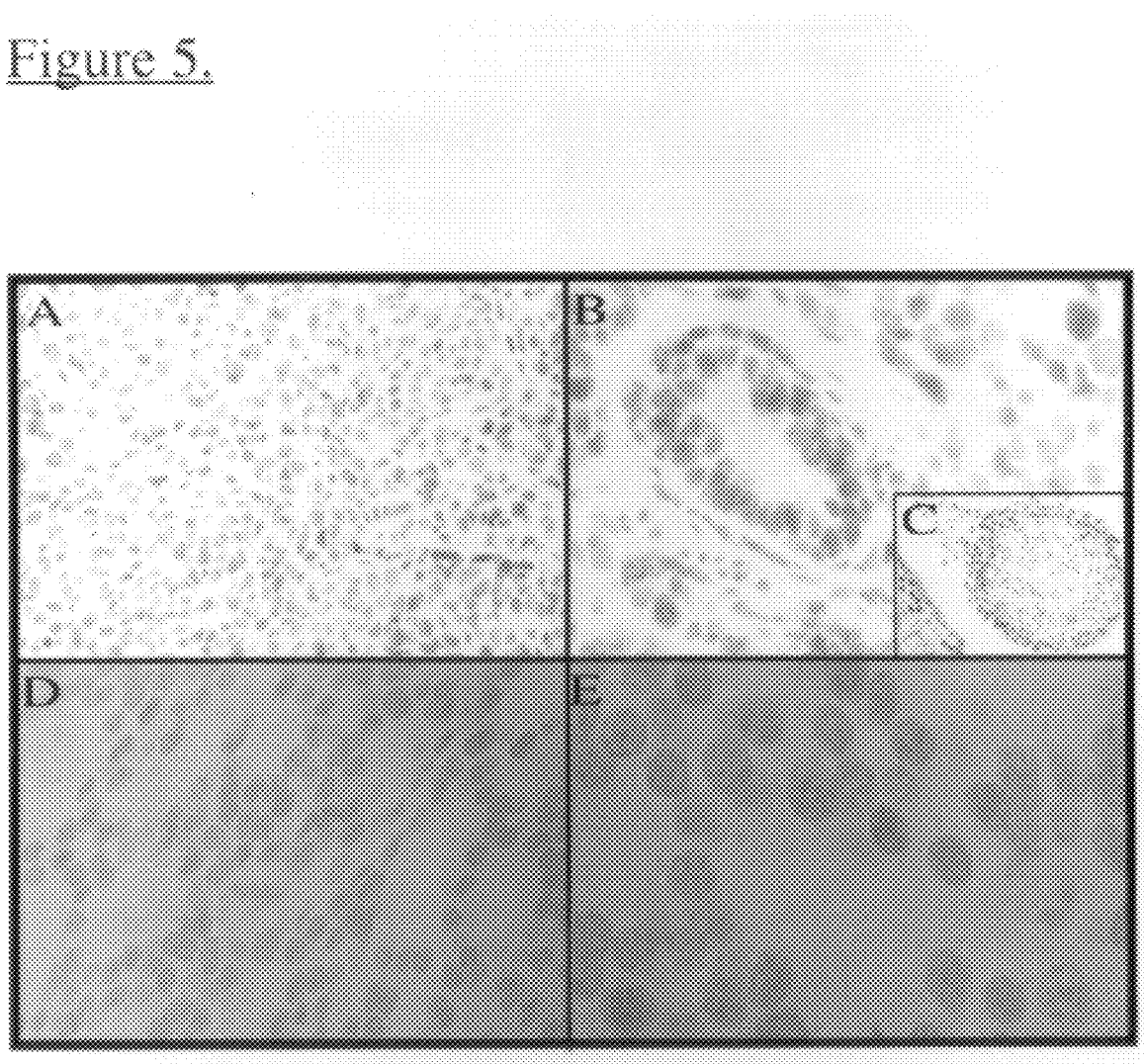
FIG. 5 comprising panels A to E, contains immunohistochemical analysis of androgen receptor expression in mouse and human prostate cancer. Paraffin sections were stained with Ab-U402. Brown regions indicate immunoreactivity. Counterstain is eosin. A. Poorly differentiated tumor in a transgenic mouse showing heterogeneous AR staining (200 X). B. Glandular components within mouse tumors contain high percentage of nuclei displaying strong AR staining (400 X). C. Section through mouse testis as positive control for AR immunostaining (50 X). D. Poorly differentiated human prostate cancer showing heterogeneous staining for AR (250 X), and E, as in (D) (500 X).

One of the hallmarks of human prostate cancer is the rapid progression of the disease following failure of hormonal therapies, indicative of androgen-independent tumor growth. Although the relationship between the loss of functional androgen receptor (AR) and the progression to androgen independence remains to be established, AR heterogeneity is often observed in human prostate cancer (Tilley, Lim-Tio, Horsfall, Aspinall, Marshall, & Skinner, 1994) and has been proposed as a response predictor for hormonal therapy (Sadi & Barrack, 1993). To determine the AR status of the tumors in mouse 8079, immunohistochemical analysis was performed using the U402 antibody specific to the NH2 terminal of AR (Husmann, Wilson, McPhaul, Tilley, & Wilson, 1990; Tilley, et al., 1994). Intense nuclear staining was observed in well differentiated epithelium with more than 70% of epithelial cell nuclei stained for AR. Surrounding stromal components showed heterogeneous staining, with smooth muscle cell nuclei also positive for AR. The normal glandular components adjacent to or within tumors contained a higher percentage of nuclei stained for AR with a greater intensity of staining compared to glands in normal tissues (FIG. 4B). In contrast, the poorly differentiated tumors showed marked heterogeneity of staining, with only 5% of tumor nuclei immunoreactive for AR (FIGS. 5A, B). The intensity of staining in the AR positive cell nuclei, however, was only slightly reduced from that of the normal glands. Similar patterns of AR staining are observed in human prostate carcinoma (Tilley, et al., 1994) as illustrated by the poorly differentiated stage D2 tumor shown in FIGS. 5D and 5E.

Figure 6:
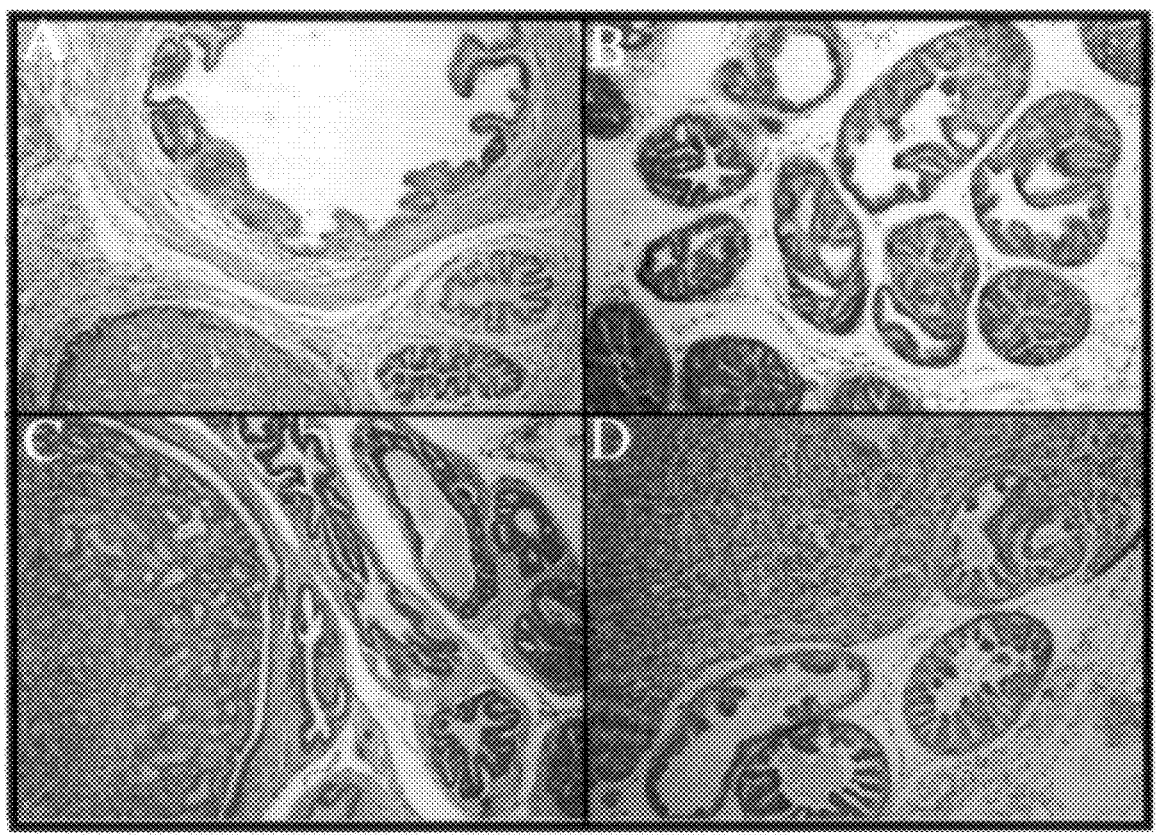
FIG. 6 comprising panels A to D, contains histological analysis of prostate tumors in PB-Tag mice line 8247. Paraffin sections were stained with hematoxylin and eosin. A. Section through mouse dorsolateral prostate of F2 male 9288 at age 10 weeks shows glands with intraepithelial hyperplasia (40 X). B. Section through dorsolateral prostate of F1 male 8866 at age 22 weeks shows predominantly hyperplastic glandular epithelium (40 X). C. Section through dorsolateral prostate of F0 male 8247 at age 40 weeks shows cribrifrom and flattened ducts with poorly differentiated adenocarcinoma (40 X). D. Section through dorsolateral prostate of F1 male 8484 at age 20 weeks shows poorly differentiated invasive adenocarcinoma with few remaining ductal structures.
Figure 7:
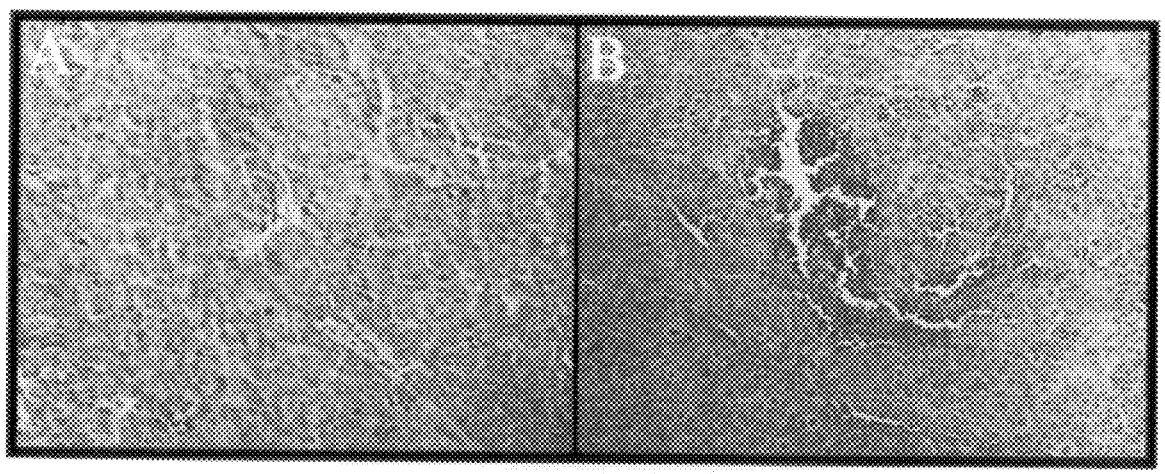
FIG. 7 comprising panels A and B, contains histological analysis of metastatic prostate cancer in PB-Tag mice line 8247. A. Section through primary tumor of dorsolateral prostate of male 1453 at age 10 weeks shows poorly differentiated invasive adenocarcinoma with few remaining ductal structures. B. Section through prostate cancer metastasis in lymph node from male 1453.
Figure 9Q:
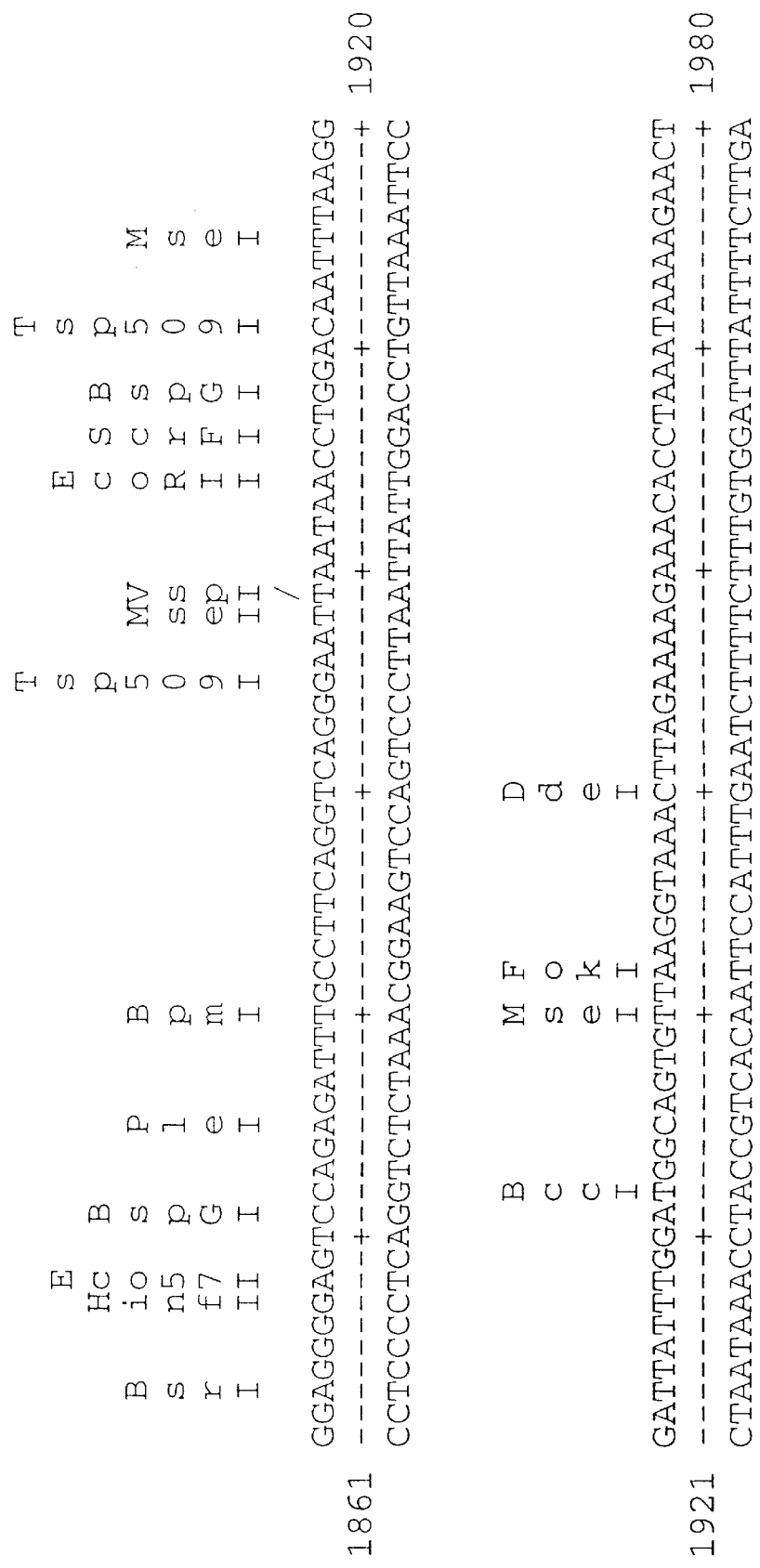
FIG. 9 contains the complete nucleotide sequence (SEQ ID NO: 2) and restriction enzyme map of the SV40 genome. The structural gene encoding the large T and small t antigen oncoproteins starts from the ATG codon at nucleic acid 82 and terminates at the TAA codon at nucleic acid 603 for the small t antigen and at nucleic acid 2552 for the large T antigen. The alternative splice sites are indicated.
Figure 9Y:
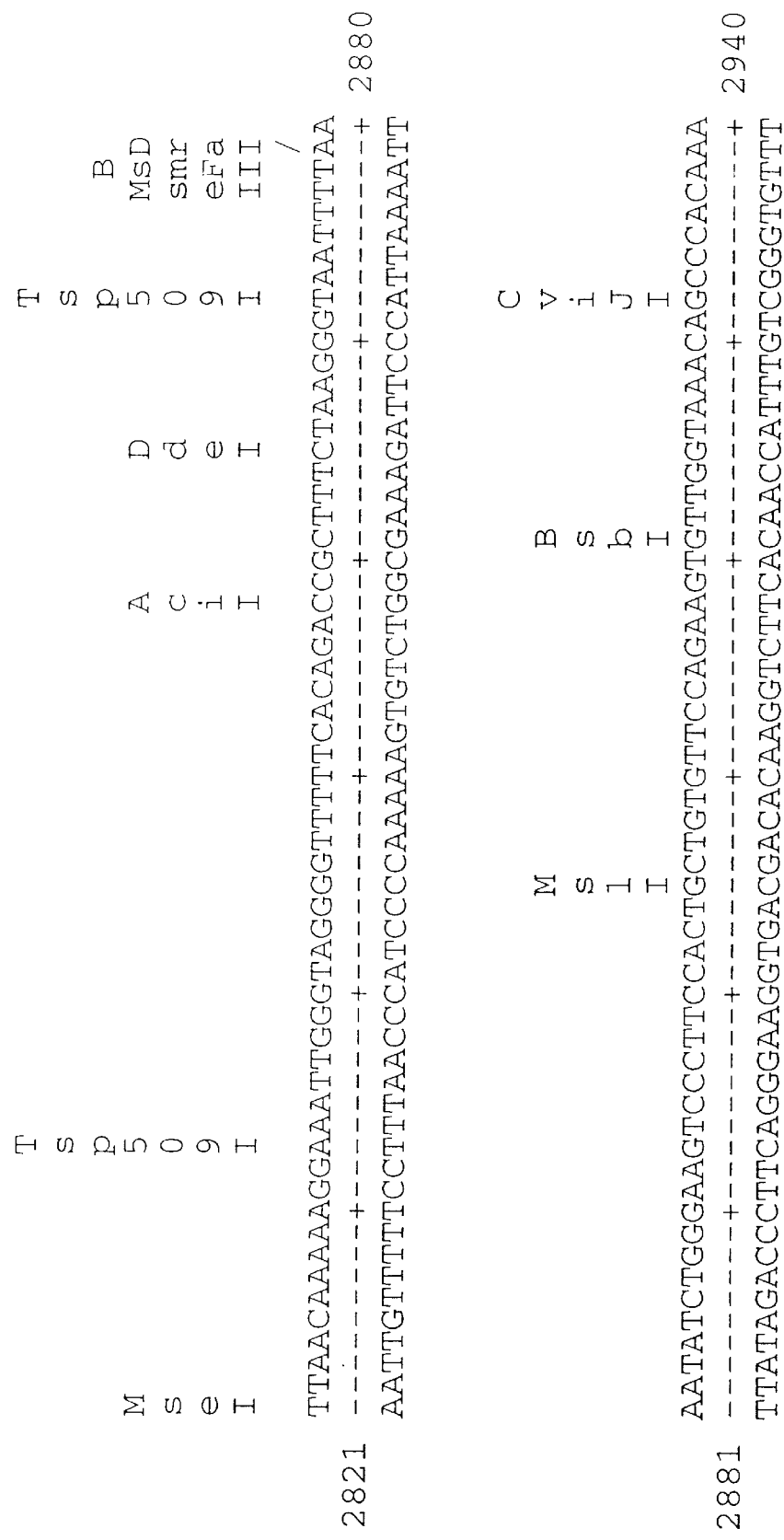
Figure 9K:
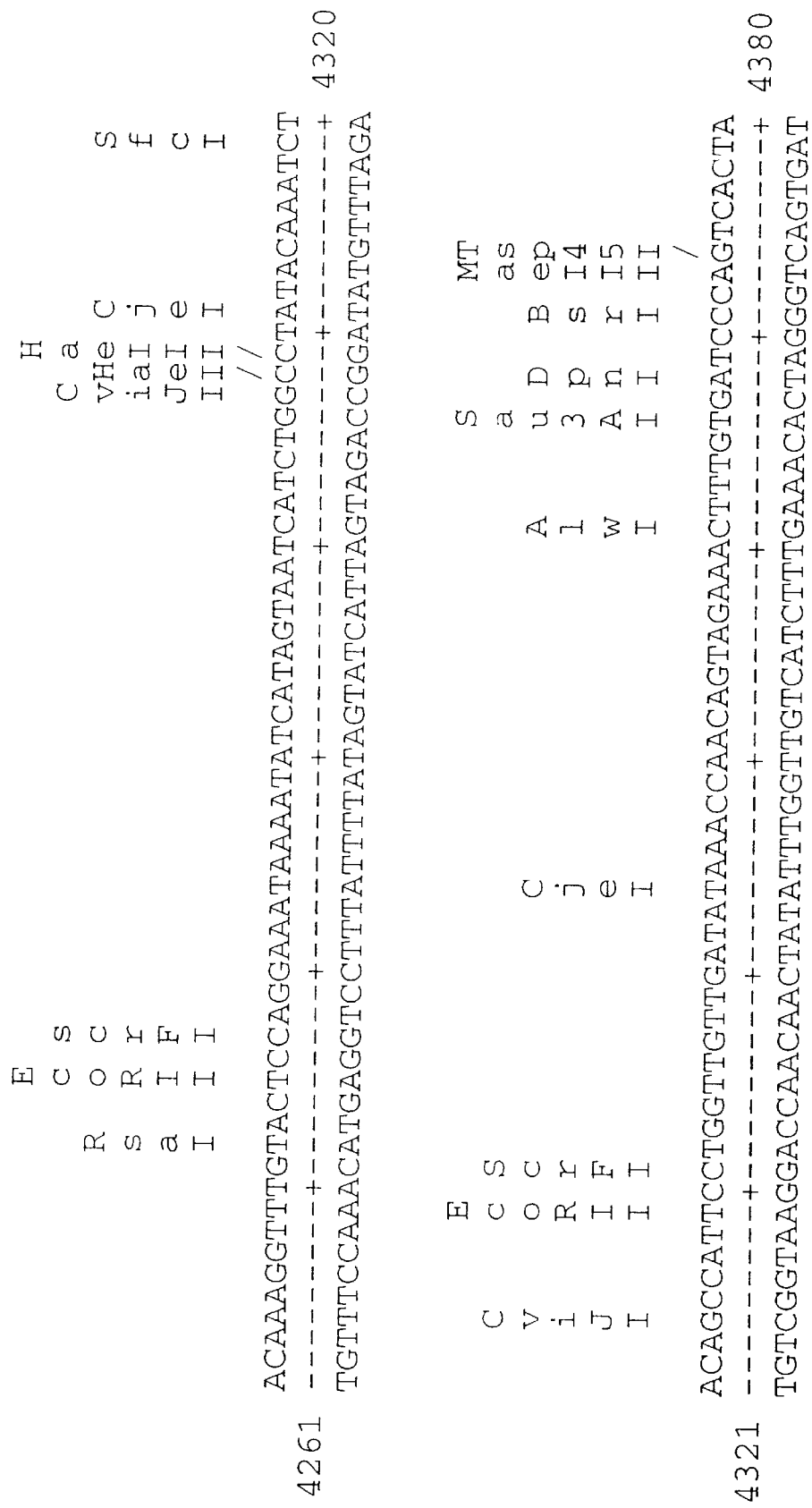
Figure 9O:
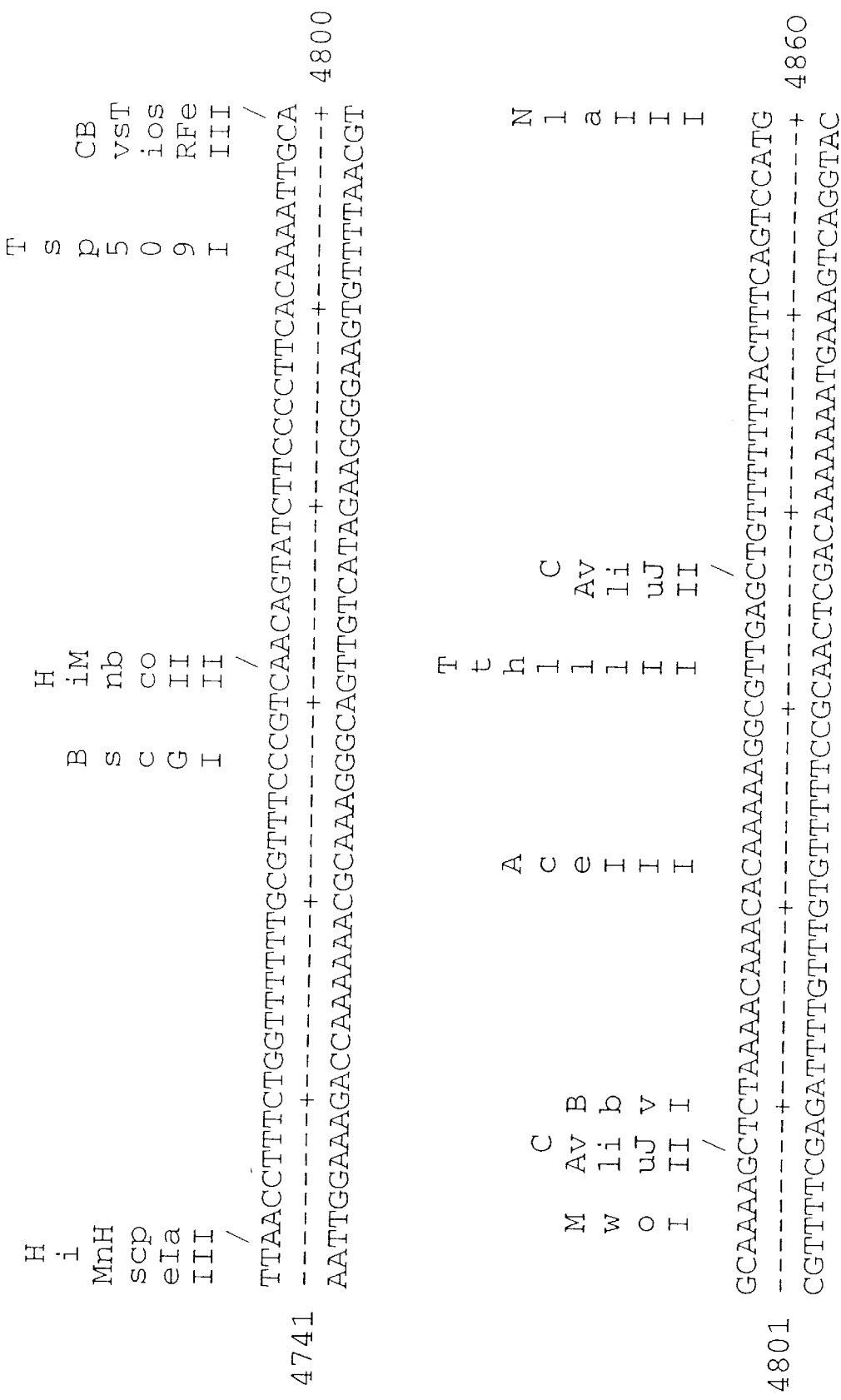

In addition to founder male 8079, prostate cancer has been detected in male offspring of a transgenic line established from founder male 8247,generated in the C57B1/6 inbred strain. When maintained in a pure C57B1/6 background, male progeny of line 8247 reproducibly display focal and invasive adenocarcinoma of the prostate by 20 weeks. A developmental study of the pathology in line 8247 has shown that intraepithelial hyperplasia can be detected in males by 10 weeks of age (FIG. 6A), and by 22 weeks of age nearly all prostatic glands are hyperplastic (FIG. 6B). Prostate glands that contain many cribriform structures in addition to adenocarcinoma can be detected in males as old as 40 weeks of age (FIG. 6C) and invasive adenocarcinoma is detected as early as 20 weeks of age in this line (FIG. 6D). When transgenic line 8247 is maintained by C57Bl/6×FVB crosses, male offspring reproducibly rapidly develop large adenocarcinomas by 20 weeks of age with metastasis to the lymph nodes. Histologic characterization of the primary tumors and metastasis is shown in FIG. 7. The establishment of additional breeding lines that display prostate cancer demonstrates the reproducibility of the transgenic strategy. Since no other pathology has been observed to date in these mice, this confirms the tissue-specificity of the PB-targeting system.

SUMMARY OF THE DISCLOSURE

In summary of this disclosure, the rPB promoter has been used to target expression of the SV40 early region genes (Tag) specifically to the prostate of transgenic mice. These mice develop epithelial hyperplasia and adenocarcinoma of the prostate with metastasis, that histologically resemble advanced human prostate cancers, as early as 10 weeks of age. The tumors display elevated levels of nuclear p53 and heterogenous androgen receptor expression. Expression of Tag was found to be restricted to the prostatic epithelium. The rPB promoter appears to be unique in its ability to target developmentally- and hormonally-regulated expression of a heterologous gene specifically to the prostate. The ability to induce prostatic disease in a transgenic mouse as a consequence of specifically targeted oncogene expression provides a novel animal model system with which to study prostate cancer and for the evaluation of strategies for the treatment and prevention of prostate cancer including gene therapy. Modifications are possible within the scope of this invention.

REFERENCES

1. Adam, J. M., & Cory, S. (1991). Transgenic models of tumor development. Science, 254, 1161–1167.
2. Aprikian, A. G., Sarkis, A. S., Fair, W. R., Zhang, Z.-F., Fuks, Z., & Cordon-Caro, C. (1994). Immunohistochemical determination of p53 protein nuclear accumulation in prostatic adenocarcinoma. Journal Urology, 151, 1276–1280.
3. Berry, S. J., Coffey, D. S., & Ewing, L. L. (Ed.). (1984). A comparison of human and canine benign prostatic hyperplasia. Berlin: Congressduck.

4. Bogden. A. E., Taylor, J. E., Moreau, J. P., & Coy, D. H. (1990). Treatment of R-3327 prostate tumors with a somatostatin analogue (somatuline) as adjuvant therapy following surgical castration. Cancer Res., 50(9), 2646–2650.
5. Bookstein, R., Rio, P., Madreperla, S. A., Hong, F., Allred, C., Grizzle, W. E., & Lee, W. H. (1990). Promoter deletion and loss of retinoblastoma gene expression in human prostate carcinoma. Proc. Natl. Acad. Sci. USA 87(19), 7762–7766.
6. Bosland, M. C., & Prinsen, M. K. (1990). Induction of dorsolateral prostate adenocarcinoma and other accessory sex gland lesions in male wistar rats by a single administration of N-methyl-N-nitrosourea, 7,12-dimethylbenz(a)anthracene, and 3,2'-dimethyl-4-aminobiphenyl after sequential treatment with cyproterone acetate and testosterone propionate. Cancer Res., 50, 691–699.
7. Bosland, M. C., Prinsen, M. K., Dirksen, T. J. M., & Spit, B. J. (1990). Characterization of adenocarcinoma of the dorsolateral prostate induced in wistar rats by N-methyl-N-nitrosourea, 7,12 dimethylbenz(a)anthracene, and 3,2'-dimethyl-4-aminobiphenyl, following sequential treatment with cyproterone acetate and testosterone propionate. Cancer Res., 50, 700–709.
8. Brinster, R. L., Chen, H. Y., Messing, A., Van Dyke, T., Levine, A. J., & Palmiter, R. D. (1984). Transgenic mice harboring SV40 T-antigen genes develop characteristic brain tumors. Cell, 37, 367–379.
9. Buttyan, R., & Slawin, K. (1993). Rodent models for targeted oncogenesis of the prostate gland. Cancer and Metastasis Rev., 12, 11–19.
10. Carroll, A. G., Voeller, H. J., Sugars, L. & Gelmann, E. P. (1993). p53 oncogene mutations in three human prostate cancer cell lines. Prostate, 23(2), 123–134.
11. Choi, Y., Lee, I., & Ross, S. R. (1988). Requirement for the simian virus 40 small antigen in tumorigenesis in transgenic mice. Mol. Cell Biol., 8(8), 3382–3390.
12. Cooke, D. B., Quarmby, V. E., Mickey, D. D., Isaacs, J. T., & French, F. S. (1988). Oncogene expression in prostate cancer: dunning r3327 rat dorsal prostatic adenocarcinoma system. Prostate, 13(4), 263–272.
13. DeCaprio, J. A., Ludlow, J. W., Figge, J., Shew, J.-Y., Huang, C.-M., Lee, W.-H., Marsilio, E., Paucha, E., & Livingston, D. M. (1988). SV40 large tumor antigen forms a specific complex with the product of the retinoblastoma susceptibility gene. Cell 17, 275–283.
14. Dodd, J. G., Sheppard, P. C., & Matusik, R. J. (1983). Characterization and cloning of highly abundant mRNAs of the rat dorsal prostate. J. Biol. Chem., 258, 10731–10737.
15. Donjacour, A. A., Rosales, A., Higgins, S. J., & Cunha, G. R. (1990). Characterization of antibodies to androgen-dependent secretory proteins of the mouse dorsolateral prostate. Endocrinology, 1343–1354.
16. Frost, J. A., Alberts, A. S., Sontag, E., Guan, K., Mumby, M. C., & Feramisco, J. R. (1994). Simian virus 40 small t antigen cooperates with mitogen activated kinases to stimulate AP-1 activity. Molecular and Cellular Biol., 14, 6244–6252.
17. Greenberg, N. M., DeMayo, F. J., Sheppard, P. C., Barrios, R., Lebovits, R., Finegold, M., Angelopolou, R., Dodd, J. G., Duckworth, M. L., Rosen, J. M., & Matusik, R. J. (1994). The rat probasin gene promoter directs hormonally- and developmentally-regulated expression of a heterologous gene specifically to the prostate in transgenic mice. Mol. Endocrinol., 8, 230–239.
18. Habenicht, U. F., el-Etreby, M. F., Lewis, R., Ghoniem, & Roberts, J. (1989). Induction of metachromasia in experimentally induced hyperplastic/hypertrophic changes in the prostate of the cynomolgus monkey (Macaca fascicularis). J. Urol., 142, 1624–1626.
19. Hanahan, D. (1985). Heritable formation of pancreatic β-cell tumors in transgenic mice expressing recombinant insulin/simian virus 40 oncogenes. Nature, 315, 115–122.
20. Husmann, D. A., Wilson, C. M., McPhaul, M. J., Tilley, W. D., & Wilson, J. D. (1990). Antipeptide antibodies to two distinct regions of the androgen receptor localize the receptor protein to the nuclei of target cells in the rat and human prostate. Endocrinology, 126, 2359–2368.
21. Isaacs, W. B., Carter, B. S., & Ewing, C. M. (1991). Wild-type p53 suppresses growth of human prostate cancer cells containing mutant p53 alleles. Cancer Res., 51(17), 4716–4720.
22. Lane, D. P., & Crawford, L. V. (1979). T-antigen is bound to host proteins in SV40-transformed cells. Nature, 278, 261–263.
23. Levine, A. J., & Momand, J. (1990). Tumor suppressor genes: the p53 and retinoblastoma sensitivity genes and gene products. Biochem. Biophys. Acta. 1032(1), 119–136.
24. Levine, A. J., Momand, J., & Finlay, C. A. (1991). The p53 tumor suppressor gene. Nature, 351(6326), 453–456.
25. Linzer, D. I. H., & Levine, A. J. (1979). Characterization of a 54 K dalton cellular SV40 tumor antigen present in SV40-transformed cells and uninfected embryonal carcinoma cells. Cell, 17, 43–52.
26. Marculakou, I. G., Anver, M., Garrett, L. & Green, J. E. (1994). Prostate and mammary adenocarcinoma in transgenic mice carrying a C3(1) simian virus 40 large tumor antigen fusion gene. Proc. Natl. Acad. Sci. USA, 91, 11236–11240.
27. Matusik, R. J., Kreis, C., McNicol, P., Sweetland, R., Mullin, C., Fleming, W. H., & Dodd, J. G. (1986). Regulation of prostatic genes: Roles of androgens and zinc in expression. J. Biochem. Cell Biology, 64, 601–607.
28. Muller, W. J., Lee, F. S., Dickson, C., Peters, G., Pattengale, P., & Leder, P. (1990). The int-2 gene product acts as an epithelial growth factor in transgenic mice. EMBO J., 9(3), 907–913.
29. Noble, R. L. (1977). The development of prostatic adenocarcinoma in Nb rats following prolonged sex hormone administration. Cancer Research, 37, 1927–1931.
30. Ornitz, D. M., Moreadith, R. W., & Leder, P. (1991). Binary system for regulating transgene expression in mice: Targeting int-2 gene expression with yeast GAL4/UAS control elements. Proc. Natl. Acad. Sci. USA, 88, 698–702.
31. Pallas, D. C., Shahrik, L. K., Martin, B. L., Jaspers, S., Miller, T. B., Brautigan, D. L., & Roberts, T. M. (1990). Polyoma small and middle T antigens and SV40 small t antigen form stable complexes with protein phosphatase 2A. Cell, 60, 167–176.
32. Pollard, M. (1973). Spontaneous adenocarcinomas in aged germfree Wistar rats. J. Natl. Cancer Inst., 51, 1235–1241.
33. Pollard, M., & Luckert, P. H. (1987). Autochthonous prostate adenocarcinomas in Lobund-Wistar rats: a model system. Prostate, 11(3), 219–227.
34. Pollard, M., Luckert, P. H. & Snyder, D. L,. (1989). The promotional effect of testosterone on induction of prostate cancer in MNU-sensitized L-W rats. Cancer Lett, 45(3), 209–212.
35. Quartin, R. S., Cole, C. N., Pipas, J. M., & Levine, A. J. (1994). The amino-terminal functions of the simian virus 36. Rennie P. S., Bruchovsky, N., Leco, K. J., Sheppard, P. C., McQueen, S. A., Cheng, H., Snoek, R., Hamel, A., Bock, M. E., MacDonald, B. S., Nickel, B. E., Chang, C., Liao, S., Cattini, P. A., & Matusik, R. J. (1993). Characterization of two cis-acting DNA elements involved in the androgen regulation of the probasin gene. Mol. Endocrinol., 7, 23–36.
37. Riegman P. H., Vlietstra, R. J., van, d.K.J.A., Romijn, J. C., & Trapman, J. (1989). Characterization of the prostate-specific antigen gene: a novel human kallikrein-like gene. Biochem. Biophys. Res. Commun. 159(1), 95–102.
38. Rubin, S. J., Hallahan, D. E., Ashman, C. R., Brachman, D. G., Beckett, M. A., Virudachalam, S., Yandell, D. W., & Weichselbaum, R. R. (1991). Two prostate carcinoma cell lines demonstrate abnormalities in tumor suppressor genes. J. Surg. Oncol. 46(1). 31–36.
39. Sadi, M. V., & Barrack, E. R. (1993). Image analysis of androgen receptor immunostaining in metastatic prostate cancer. Heterogeneity as a predictor of response to hormonal therapy. Cancer, 71, 2574–2580.
40. Schaffner, D. L., Barrios, R., Shaker, M., Rajagopalan, S., Huang, S., Tindall, D. J., Young, C. Y. F., Overbeek, P. A., Lebovitz, R. M., & Lieberman, M. W. (1994). Transgenic mice carrying a PSArasT24 hybrid gene develop salivary gland and GI tract neoplasms. Laboratory Investigation, in press.
41. Shain, S. A., McCullough, B., Nitchuk, M., & Boesel, R. W., (1977). Prostate carcinogenesis in the AXC rat. Oncology, 34(3), 114–122.
42. Shain, S. A., McCullough, B., & Segaloff, A. (1975). Spontaneous adenocarcinomas of the ventral prostate of aged AXC rats. J. Natl. Cancer Inst., 55(1), 177–180.
43. Shaulsky, G., Goldfinger, N., Tosky, M. S., Levine, A. J., & Rotter, V. (1991). Nuclear locatlization is essential for the activity of p53 protein. Oncogene, 6(11), 2055–2065.
44. Shirai, T., Fukushima, S., lkawa, Y., & Ito, N. (1986). Induction of prostate carcinoma in situ at high incidence in F344 rats by a combination of 3,2'-dimethyl-4-aminobiphenyl and ethinyl estradiol. Cancer Res., 46, 6423–6426.
45. Silverberg, E. S., Boring, C. C. & Squires, T. S. (1990). Cancer Statistics. CA Cancer J. Clin. 40, 9–26.
46. Slawin, K., Kadmon, D., Park, S. H., Scardino, P. T., Anzano, M., Sporn, M. B., & Thompson, T. C. (1993). Dietary fenretinide, a synthetic retinoid, decreases the tumor incidence and the tumor mass of ras+myc-induced carcinomas in the mouse prostate reconstitution model system. Cancer Res., 53(19), 4461–4465.
47. Smith, M. S., Lechago, J., Wines, D. R., MacDonald, R. J., & Hammer, R. E. (1992). Tissue-specific expression of kallikrein family transgenes in mice and rats. DNA Cell Biol., 11(5), 345–358.
48. Sweetland, R., Sheppard, P. C., Dodd, J. G., & Matusik, R. J. (1988). Post-castration rebound of an androgen regulated prostatic gene. Mol. Cell Biochem. 84, 3–15.
49. Thalman, G. N., Anezinis, P. E., Chang, S.-M., Zhau, H. E., Kim, E., Hopwood, V. L., Pathak, S., von Eschenbach, A. C., & Chung, L. W. K. (1994). Androgen-independent cancer progression and bone metastasis in the LnCaP model of human prostate cancer. Cancer Research, 54, 2577–2581.
50. Thompson, T. C., Kadmon, D., Timme, T. L., Merz, V. W., Egawa, S., Krebs, T., Scardino, P. T., & Park, S. H. (1991). Experimental oncogene induced prostate cancer. Cancer Surv. 11, 55–71.
51. Thompson, T. C., Timme, T. L., Kadmon, D., Park, S. H., Egawa, S., & Yoshida, K. (1993a). Genetic predisposition and mesenchymal-epithelial interactions in ras+myc-induced carcinogenesis in reconstituted mouse prostate. Molecular Carcinogenesis, 7(3), 165–179.
52. Thompson, T. C., Truong, L. D., Timme, T. L., Kadmon, D., McCune, B. K., Flanders, K. C., Scardino, P. T., & Park, S. H. (1993b). Transgenic models for the study of prostate cancer. Cancer 71(3 Suppl), 1165–1171.
53. Thompson, T. T., Southgate, J., Kitchener, G., & Land, H. (1989). Multistage carcinogenesis induced by ras and myc oncogenes in a reconstituted organ. Cell, 56, 917–930.
54. Tilley, W. D., Lim-Tio, S. S., Horsfall, D. J., Aspinall, J. O., Marshall, V. R., & Skinner, J. M. (1994). Detection of discrete androgen receptor epitopes in prostate cancer by immunostaining: Measurement by color video image analysis. Cancer Research, 54, 4096–4102.
55. Timme, T. L., Park, S. H. Ren, C., Eastham, J. A., Baley, P. A., Kadmon, D., Donehower, L. A., & Thompson, T. C. (1994). The use of a novel mouse model for prostate cancer metastasis to analyze the role of p53 gene loss and alteration during progression. AACR Proceedings, 35, 584.
Tutrone, R. F. J., Ball, R. A., Ornitz, D. M., Leder, P. & Richie, J. P. (1993). Benign prostatic hyperplasia in a transgenic mouse: a new hormonally sensitive investigatory model. J. Urology, 149, 633–639.
57. Tzeng, Y. J., Guhl, E., Graessmann, M., & Graessmann, A. (1993). Breast cancer formation in transgenic animals induced by the whey acidic protein SV40 T antigen (WAP-SV-T) hybrid gene. Oncogene, 8(7), 1965–1971.
58. van, S. G. J., & Schroder, F. H. (1988). Androgen-dependent human prostate cancer in nude mice. The PC-82 tumor model. Am. J. Clin. Oncol., 2.
59. Waalkes, M. P., Rehm, S., Riggs, C. W., Bare, R. M., Devor, D. E., Poirer, L. A., Wenk, M. L., Henneman, J. R., & Balaschak, M. S. (1988). Cadmium carcinogenesis in male Wistar [Crl:(WI)BR] rats: dose-response analysis of tumor induction in the prostate and testes and at the injection site. Cancer Res., 48, 4656–4663.

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
    (A) LENGTH: 556 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: CDS
    (B) LOCATION: 467..547

(xi) SEQUENCE DESCRIPTION: SEQ ID NO: 1:

```
AAGCTTCCAC AAGTGCATTT AGCCTCTCCA GTATTGCTGA TGAATCCACA GTTCAGGTTC      60

AATGGCGTTC AAAACTTGAT CAAAAATGAC CAGACTTTAT ATTCTTACAC CAACATCTAT     120

CTGATTGGAG GAATGGATAA TAGTCATCAT GTTTAAACAT CTACCATTCC AGTTAAGAAA     180

ATATGATAGC ATCTTGTTCT TAGTCTTTTT CTTAATAGGG ACATAAAGCC CACAAATAAA     240

AATATGCCTG AAGAATGGGA CAGGCATTGG GCATTGTCCA TGCCTAGTAA AGTACTCCAA     300

GAACCTATTT GTATACTAGA TGACACAATG TCAATGTCTG TGTACAACTG CCAACTGGGA     360

TGCAAGACAC TGCCCATGCC AATCATCCTG AAAAGCAGCT ATAAAAAGCA GGAAGCTACT     420

CTGCACCTTG TCAGTGAGGT CCAGATACCT ACAGAGCTCA CACAGC ATG AGG GTC         475
                                                Met Arg Val
                                                  1

ATC CTC CTC CTG CTC ACA CTG GAT GTG CTA GGT GTC TCC AGT ATG ATG        523
Ile Leu Leu Leu Leu Thr Leu Asp Val Leu Gly Val Ser Ser Met Met
  5                  10                  15

ACA GAC AAG AAT CTC AAA AAG AAG GTAGCAGAC                              556
Thr Asp Lys Asn Leu Lys Lys Lys
 20                  25
```

(2) INFORMATION FOR SEQ ID NO:2:

(i) SEQUENCE CHARACTERISTICS:
        (A) LENGTH: 5243 base pairs
        (B) TYPE: nucleic acid
        (C) STRANDEDNESS: single
        (D) TOPOLOGY: linear (xi) SEQUENCE DESCRIPTION: SEQ ID NO:2:

```
CGCCTCGGCC TCTGAGCTAT TCCAGAAGTA GTGAGGAGGC TTTTTTGGAG GCCTAGGCTT      60

TTGCAAAAAG CTTTGCAAAG ATGGATAAAG TTTTAAACAG AGAGGAATCT TTGCAGCTAA     120

TGGACCTTCT AGGTCTTGAA AGGAGTGCCT GGGGGAATAT TCCTCTGATG AGAAAGGCAT     180

ATTTAAAAAA ATGCAAGGAG TTTCATCCTG ATAAAGGAGG AGATGAAGAA AAAATGAAGA     240

AAATGAATAC TCTGTACAAG AAAATGGAAG ATGGAGTAAA ATATGCTCAT CAACCTGACT     300

TTGGAGGCTT CTGGGATGCA ACTGAGGTAT TTGCTTCTTC CTTAAATCCT GGTGTTGATG     360

CAATGTACTG CAAACAATGG CCTGAGTGTG CAAAGAAAAT GTCTGCTAAC TGCATATGCT     420

TGCTGTGCTT ACTGAGGATG AAGCATGAAA ATAGAAAATT ATACAGGAAA GATCCACTTG     480

TGTGGGTTGA TTGCTACTGC TTCGATTGCT TTAGAATGTG GTTTGGACTT GATCTTTGTG     540

AAGGAACCTT ACTTCTGTGG TGTGACATAA TTGGACAAAC TACCTACAGA GATTTAAAGC     600

TCTAAGGTAA ATATAAAATT TTTAAGTGTA TAATGTGTTA AACTACTGAT TCTAATTGTT     660

TGTGTATTTT AGATTCCAAC CTATGGAACT GATGAATGGG AGCAGTGGTG GAATGCCTTT     720

AATGAGGAAA ACCTGTTTTG CTCAGAAGAA ATGCCATCTA GTGATGATGA GGCTACTGCT     780

GACTCTCAAC ATTCTACTCC TCCAAAAAAG AAGAGAAAGG TAGAAGACCC CAAGGACTTT     840
```

```
CCTTCAGAAT TGCTAAGTTT TTTGAGTCAT GCTGTGTTTA GTAATAGAAC TCTTGCTTGC    900

TTTGCTATTT ACACCACAAA GGAAAAAGCT GCACTGCTAT ACAAGAAAAT TATGGAAAAA    960

TATTCTGTAA CCTTTATAAG TAGGCATAAC AGTTATAATC ATAACATACT GTTTTTCTT   1020

ACTCCACACA GGCATAGAGT GTCTGCTATT AATAACTATG CTCAAAAATT GTGTACCTTT  1080

AGCTTTTTAA TTTGTAAAGG GGTTAATAAG GAATATTTGA TGTATAGTGC CTTGACTAGA  1140

GATCCATTTT CTGTTATTGA GGAAAGTTTG CCAGGTGGGT TAAAGGAGCA TGATTTTAAT  1200

CCAGAAGAAG CAGAGGAAAC TAAACAAGTG TCCTGGAAGC TTGTAACAGA GTATGCAATG  1260

GAAACAAAAT GTGATGATGT GTTGTTATTG CTTGGGATGT ACTTGGAATT TCAGTACAGT  1320

TTTGAAATGT GTTTAAAATG TATTAAAAAA GAACAGCCCA GCCACTATAA GTACCATGAA  1380

AAGCATTATG CAAATGCTGC TATATTTGCT GACAGCAAAA ACCAAAAAAC CATATGCCAA  1440

CAGGCTGTTG ATACTGTTTT AGCTAAAAAG CGGGTTGATA GCCTACAATT AACTAGAGAA  1500

CAAATGTTAA CAAACAGATT TAATGATCTT TTGGATAGGA TGGATATAAT GTTTGGTTCT  1560

ACAGGCTCTG CTGACATAGA AGAATGGATG GCTGGAGTTG CTTGGCTACA CTGTTTGTTG  1620

CCCAAAATGG ATTCAGTGGT GTATGACTTT TTAAAATGCA TGGTGTACAA CATTCCTAAA  1680

AAAAGATACT GGCTGTTTAA AGGACCAATT GATAGTGGTA AAACTACATT AGCAGCTGCT  1740

TTGCTTGAAT TATGTGGGGG GAAAGCTTTA AATGTTAATT TGCCCTTGGA CAGGCTGAAC  1800

TTTGAGCTAG GAGTAGCTAT TGACCAGTTT TTAGTAGTTT TTGAGGATGT AAAGGGCACT  1860

GGAGGGGAGT CCAGAGATTT GCCTTCAGGT CAGGAATTA ATAACCTGGA CAATTTAAGG  1920

GATTATTTGG ATGGCAGTGT TAAGGTAAAC TTAGAAAAGA AACACCTAAA TAAAAGAACT  1980

CAAATATTTC CCCCTGGAAT AGTCACCATG AATGAGTACA GTGTGCCTAA AACACTGCAG  2040

GCCAGATTTG TAAAACAAAT AGATTTTAGG CCCAAAGATT ATTTAAAGCA TTGCCTGGAA  2100

CGCAGTGAGT TTTTGTTAGA AAAGAGAATA ATTCAAAGTG GCATTGCTTT GCTTCTTATG  2160

TTAATTTGGT ACAGACCTGT GGCTGAGTTT GCTCAAAGTA TTCAGAGCAG AATTGTGGAG  2220

TGGAAAGAGA GATTGGACAA AGAGTTTAGT TTGTCAGTGT ATCAAAAAAT GAAGTTTAAT  2280

GTGGCTATGG GAATTGGAGT TTTAGATTGG CTAAGAAACA GTGATGATGA TGATGAAGAC  2340

AGCCAGGAAA ATGCTGATAA AAATGAAGAT GGTGGGGAGA GAACATGGA AGACTCAGGG   2400

CATGAAACAG GCATTGATTC AGAGTCCCAA GGCTCATTTC AGGCCCCTCA GTCCTCACAG  2460

TCTGTTCATG ATCATAATCA GCCATACCAC ATTTGTAGAG GTTTTACTTG CTTTAAAAAA  2520

CCTCCCACAC CTCCCCCTGA ACCTGAAACA TAAAATGAAT GCAATTGTTG TTGTTAACTT  2580

GTTTATTGCA GCTTATAATG GTTACAAATA AAGCAATAGC ATCACAAATT TCACAAATAA  2640

AGCATTTTTT TCACTGCATT CTAGTTGTGG TTTGTCCAAA CTCATCAATG TATCTTATCA  2700

TGTCTGGATC CCCAGGAAGC TCCTCTGTGT CCTCATAAAC CCTAACCTCC TCTACTTGAG  2760

AGGACATTCC AATCATAGGC TGCCCATCCA CCCTCTGTGT CCTCCTGTTA ATTAGGTCAC  2820

TTAACAAAAA GGAAATTGGG TAGGGGTTTT TCACAGACCG CTTTCTAAGG GTAATTTTAA  2880

AATATCTGGG AAGTCCCTTC CACTGCTGTG TTCCAGAAGT GTTGGTAAAC AGCCCACAAA  2940

TGTCAACAGC AGAAACATAC AAGCTGTCAG CTTTGCACAA GGGCCCAACA CCCTGCTCAT  3000

CAAGAAGCAC TGTGGTTGCT GTGTTAGTAA TGTGCAAAAC AGGAGGCACA TTTTCCCCAC  3060

CTGTGTAGGT TCCAAAATAT CTAGTGTTTT CATTTTTACT TGGATCAGGA ACCCAGCACT  3120

CCACTGGATA AGCATTATCC TTATCCAAAA CAGCCTTGTG GTCAGTGTTC ATCTGCTGAC  3180

TGTCAACTGT AGCATTTTTT GGGGTTACAG TTTGAGCAGG ATATTTGGTC CTGTAGTTTG  3240
```

```
CTAACACACC CTGCAGCTCC AAAGGTTCCC CACCAACAGC AAAAAAATGA AAATTTGACC      3300

CTTGAATGGG TTTTCCAGCA CCATTTTCAT GAGTTTTTTG TGTCCCTGAA TGCAAGTTTA      3360

ACATAGCAGT TACCCCAATA ACCTCAGTTT TAACAGTAAC AGCTTCCCAC ATCAAAATAT      3420

TTCCACAGGT TAAGTCCTCA TTTAAATTAG GCAAAGGAAT TCTAGCCACA CTGTAGCAAG      3480

GCAGTTGTTC TTTGTCTGGA GAGTCATCTG TAAACTGTTT TTCAGCTGCT AAGCTTTTAC      3540

TTAAGCCTTT TTGATGTTCA TCAGGATTGC CCATTTGAGG ATTTAAAAAG CACTCCACCT      3600

CAGTGAAGCT GTCTACTCCA GTTTTAACTC CTAGAACTTC TATTCCTCCT TTTATGACGA      3660

GCTTTGGCAC TTGCACTGGT TCCTTTGGTT TTTTGGGAGC TGCCCCTGGA CAACTTCCTT      3720

TTCTTTTTGT TGGGGCCATC TTCATAAGCT TTTAGAGCAG AAGTAACACT TCCGTACAGG      3780

CCTAGAAGTA AAGGCAACAT CCACTGAGGA GCAGTTCTTT GATTTGCACC ACCAGGAGCC      3840

TCAAATTTTT CAATAAATTC ACCTGACTGC ACATTAGGAC TTTGGCTTTG AGCTTCCCAC      3900

CTCTCAGTTA CTTGCTGAAT ACTGTCTGCT TCATCAATAT TATCATAGGT GTGCCCAAAT      3960

GATATTTGCA ACCCTTCCCT GTTGGCTACT TGTCTCACCA TTGTAGGCCT AATGGGAGAC      4020

AAAGTAGAGT AGTAATCTTG TAAAGAGTTA TACCAATTAA CAGGAGCATT AATTACTGTC      4080

CAAGTAGTTT CCTCTAAAAA CCTTGCCAAA CTGTCCCTTA AATATCTTTG GGTTCTTCTT      4140

TCAAGCTCCT GTGAGGTGAG CCTAGGAATG TCATTTTGTA TTACACGCCA AAAAGCTTGA      4200

GAAATGGCAT TAAAAAGTGT TGGACCCCAA TGTCTGGGGT CAAGATACTG AACACTGTGA      4260

ACAAAGGTTT GTACTCCAGG AAATAAAATA TCATAGTAAT CATCTGGCCT ATACAAATCT      4320

ACAGCCATTC CTGGTTGTTG ATATAAACCA ACAGTAGAAA CTTTGTGATC CCAGTCACTA      4380

AAAAATCTAT ACCCCACTTG AGCAACAGCG CTCACACCAG TCACAGTTTG CAGTAAAGCT      4440

GCAAATCCAG CTATAGCAGC AGGAGCCCCA GATATCACAG CATAGGCCTG TGGAGTGAGG      4500

CCTATAGCAG CAATTGCCTC AGAGGTTGTT AGGCCTTCAA CAGTAGCAAC AGATGCAAGT      4560

TGCACTTCAA TTGCAGCAGC GGCCTCTCCA GCAGCAATTT CAGCTACTGA AAATCCAGTA      4620

GCAGCAGCAG CTTCAGACAC AGTAGCAATT AGGTCCCCCA ACAGTGTTAA AGCAGCACCC      4680

ATGGACCTGA AATAAAAGAC AAAAAGACTA AACTTACCAG TTAACTTTCT GGTTTTTCAG      4740

TTAACCTTTC TGGTTTTTTG CGTTTCCCGT CAACAGTATC TTCCCCTTCA CAAAATTGCA      4800

GCAAAAGCTC TAAAACAAAC ACAAAAAGGC GTTGAGCTGT TTTTTTACTT TCAGTCCATG      4860

ACCTACGAAC CTTAACGGAG GCCTGGCGTG ACAGCCGGCG CAGCACCATG GCCTGAAATA      4920

ACCTCTGAAA GAGGAACTTG GTTAGGTACC TTCTGAGGCG GAAAGAACCA GCTGTGGAAT      4980

GTGTGTCAGT TAGGGTGTGG AAAGTCCCCA GGCTCCCCAG CAGGCAGAAG TATGCAAAGC      5040

ATGCATCTCA ATTAGTCAGC AACCAGGTGT GGAAAGTCCC CAGGCTCCCC AGCAGGCAGA      5100

AGTATGCAAA GCATGCATCT CAATTAGTCA GCAACCATAG TCCCGCCCCT AACTCCGCCC      5160

ATCCCGCCCC TAACTCCGCC CAGTTCCGCC CATTCTCCGC CCCATGGCTG ACTAATTTTT      5220

TTTATTTATG CAGAGGCCGA GGC                                              5243

(2) INFORMATION FOR SEQ ID NO:3:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (xi) SEQUENCE DESCRIPTION: SEQ ID NO:3:

CCGGTCGACC GGAAGCTTCC ACAAGTGCAT TTA                                     33
```

(2) INFORMATION FOR SEQ ID NO:4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:4:

AGGCATTCCA CCACTGCTCC CATTCATC        28

What we claim is:

1. A transgenic mouse susceptible to prostate tumor formation having genomically-integrated in the mouse a nucleic acid molecule, comprising:

a first segment which is a 5' flanking region of the rat probasin gene as shown in FIG. 8 (SEQ ID NO:1), and a second segment which is an oncogene encoding the SV40 early region-tumor antigen (Tag)(SEQ ID NO:2), said first and second segments being operatively linked such that said mouse expresses said tumor antigen specifically in the prostate of said mouse to effect tumor formation therein.

2. The transgenic mouse of claim 1 wherein said mouse has a matrix attachment region cointegrated therewith.

3. The transgenic mouse of claim 1 wherein said oncogene is that encoding the SV40 large T antigen.

4. The transgenic mouse of claim 1 wherein said oncogene is that encoding the SV40 small t antigen.

5. The transgenic mouse of claim 1 having a disease state caused by said expression of said oncogene, wherein said disease state comprises one of prostatic hyperplasia, androgen-responsive tumors or androgen-unresponsive tumors.

6. An immortal cell line derived from prostatic tissue of the transgenic mouse of claim 1 and representing a stage of progression of prostate cancer.

7. The cell line of claim 6 which represents a stage of hyperplasia.

8. The cell line of claim 6 which represents a stage of androgen-response.

9. The cell line of claim 6 which represents a stage of androgen-unresponse.

Figure 12:
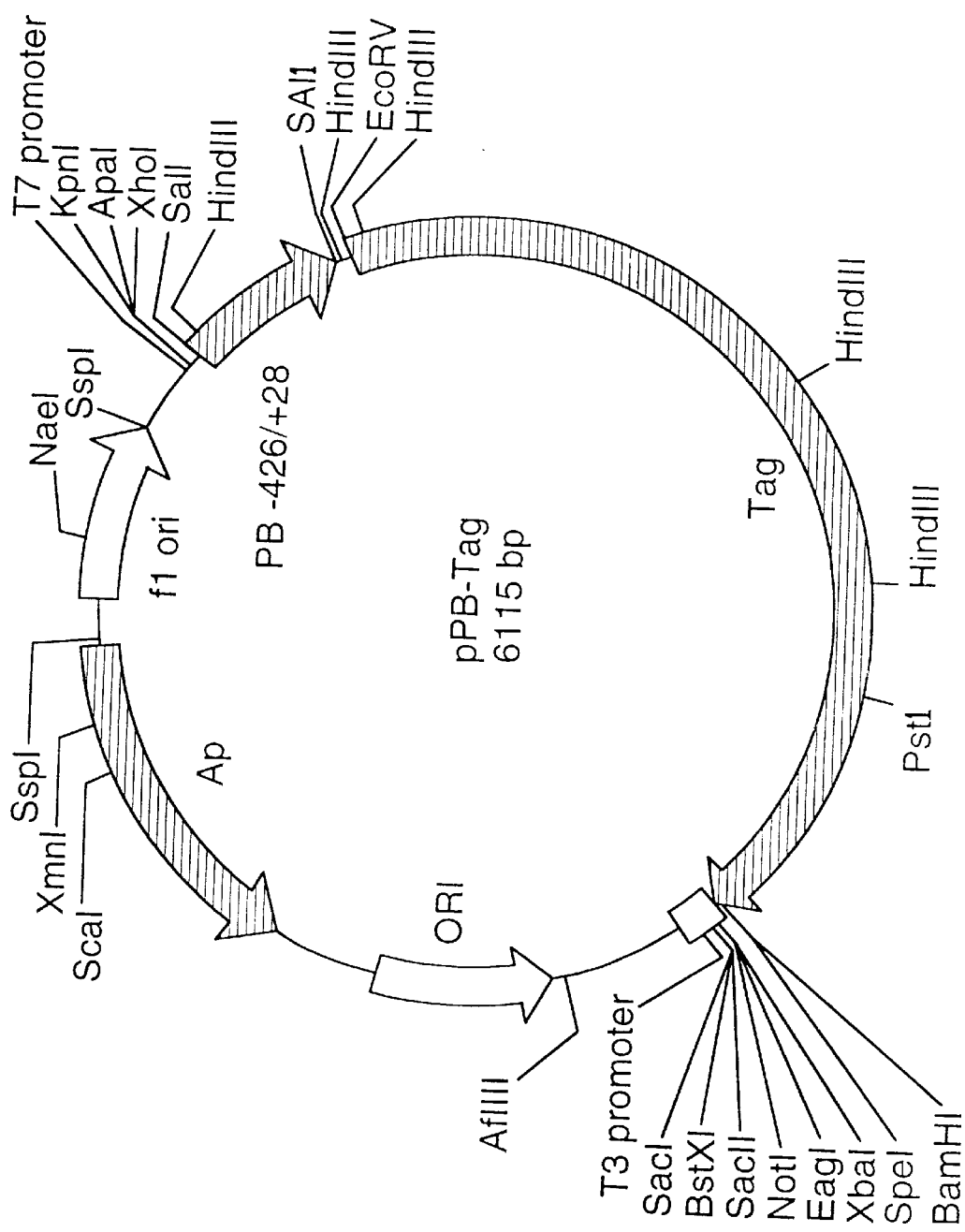
FIG. 12 is a diagrammatic representation of the plasmid pPB-Tag showing the restriction sites.

10. The plasmid pPB-Tag comprising the 5' flanking region of the rat probasin gene operatively linked to an SV40 early region tumor antigen, as shown in FIG. 12.

* * * * *